(12) United States Patent
Bird et al.

(10) Patent No.: US 7,189,521 B2
(45) Date of Patent: Mar. 13, 2007

(54) CLAUDIN POLYPEPTIDES, POLYNUCLEOTIDES, AND METHODS OF MAKING AND USE THEREOF

(75) Inventors: Timothy A. Bird, Bainbridge Island, WA (US); Adel Youakim, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 98 days.

(21) Appl. No.: 10/965,972

(22) Filed: Oct. 15, 2004

(65) Prior Publication Data

US 2005/0266421 A1 Dec. 1, 2005

Related U.S. Application Data

(63) Continuation of application No. PCT/US03/16052, filed on May 20, 2003.

(60) Provisional application No. 60/382,040, filed on May 20, 2002.

(51) Int. Cl.
*G01N 33/53* (2006.01)
*C07K 1/00* (2006.01)
*C12P 21/06* (2006.01)

(52) U.S. Cl. .................. 435/7.1; 530/350; 435/69.1

(58) Field of Classification Search ................ 530/350; 512/12; 435/69.1, 7.1
See application file for complete search history.

(56) References Cited

U.S. PATENT DOCUMENTS

2004/0219521 A1* 11/2004 Tang et al. .................. 435/6

FOREIGN PATENT DOCUMENTS

| WO | WO 00/26360 | 5/2000 |
|---|---|---|
| WO | WO 02/14499 A2 | 2/2002 |
| WO | WO 02/099062 A2 | 12/2002 |
| WO | WO 03/008553 A2 | 1/2003 |
| WO | WO 03/023013 A2 | 3/2003 |

OTHER PUBLICATIONS

STIC seqeunce search alignment data, protein search using sw model, Run on May 1, 2006, Title 10965972-6, pp. 1-3.*
Database NCBI Sequence Viewer, AN:AAH16047, 'National Institutes of Health, Mammalian Gene Collection (MGC), Cancer Genomics Office, National Cancer Institute', Gene Sequence, Oct. 22, 2001.
Katoh and Katoh, "CLDN23 gene, frequently down-regulated in intestinal-type gastric cancer, is a novel member of the CLAUDIN gene family," *Int J Mol Med* 11(6):683-689, Jun. 2003.
Morita et al.:"Claudin multigene family encoding four-transmembrane domain protein components of tight junction strands" Proc. Natl. Acad. Sci USA, 96:511-516; 1999.
EMBL Database Accession No. AK009330, Feb. 8, 2001.
EMBL Database Accession No. BM821052, Mar. 10, 2002.
EMBL Database Accession No. BC016047, Oct. 26, 2001.
Partial European Search Report, EP 03731300, Aug. 26, 2005.

* cited by examiner

*Primary Examiner*—Ponnathapu Achutamurthy
*Assistant Examiner*—Robert B. Mondesi
(74) *Attorney, Agent, or Firm*—Suzanne A. Sprunger; Susan E. Lingenfelter

(57) ABSTRACT

This invention relates to new members of the human Claudin polypeptide family, to methods of making such polypeptides, and to methods of using them to treat Claudin-associated conditions and to identify agents that alter Claudin polypeptide activities.

3 Claims, No Drawings

CLAUDIN POLYPEPTIDES, POLYNUCLEOTIDES, AND METHODS OF MAKING AND USE THEREOF

This application is a continuation of International Application Serial No. PCT/US03/16052, filed May 20, 2003; which designates the United States and claims the benefit under 35 U.S.C. 119(e) of U.S. provisional application Ser. No. 60/382,040, filed May 20, 2002; all of which are incorporated in their entirety by reference herein.

FIELD OF THE INVENTION

This invention relates to novel human and murine polypeptides of the Claudin polypeptide family, and to methods of making and using them.

BACKGROUND

Tight junctions, which are also called "zona occludens", form a regulated, semipermeable barrier in the intercellular spaces within sheets of epithelial or endothelial cells. The properly regulated formation of tight junctions is an important aspect of the normal development of tissues such as the skin, and maintenance of these junctions may assist in suppressing the formation and spread of tumors. Inadequate or improperly regulated epithelial or endothelial barrier function contributes to the initiation, maintenance, and exacerbation of inflammation in tissues such as the gut, lungs, and the like. Tight junctions also form a "fence" separating the apical and basolateral regions of these cells' membranes, allowing the establishment of different physiological environments on the opposite sides of a cell sheet, such as the different physiological environments required for transport of materials across the intestinal epithelium. It has also been proposed that tight junctions contain aqueous pores, with paracellular transport between the cells of an epithelial or endothelial sheet occurring through these pores. In order to develop more effective treatments for conditions involving disruption of epithelial or endothelial barrier function or unregulated transport across the epithelium or endothelium, such as inflammatory bowel disease or skin disorders such as psoriasis or contact dermatitis, the identification of proteins that play a role in tight junctions is critical in understanding and treating such diseases and disorders.

SUMMARY OF THE INVENTION

The invention is based upon the discovery of a new member of the Claudin polypeptide family, Claudin-23.

The invention provides a substantially purified or isolated polypeptide comprising, consisting essentially of, or consisting of an amino acid sequence selected from the group consisting of: (a) an amino acid sequence as set forth in SEQ ID NO:6; (b) a Claudin-23 fragment, wherein the Claudin-23 fragment consists of an extracellular loop of a Claudin-23 polypeptide; (c) a Claudin-23 fragment, wherein the Clauldin-23 fragment consists of a cytoplasmic domain of a Claudin-23 polypeptide; (d) a Claudin-23 fragment, wherein the Claudin-23 fragment consists of at least 20 contiguous amino acid of SEQ ID NO:6 or 8 and has Claudin polypeptide activity; and (e) a Claudin-23 polypeptide variant, wherein the Claudin-23 variant is at least 80%, at least 90%, at least 95%, at least 97.5%, at least 99% or at least 99.5% identical to SEQ ID NO:6 or 8 and wherein the Claudin-23 variant has Claudin-23 polypeptide activity. In one embodiment, the polypeptides of the invention consist essentially of specified portions of SEQ ID NO:6 or 8, such as amino acids 31 through 76 of SEQ ID NO:6 or amino acids 138 through 159 of SEQ ID NO:6, or variants thereof, and do not comprise any of the polypeptides disclosed in WO 02/099062, WO 03/008553, or WO 03/023013. In further embodiments, the polypeptides of the invention consist essentially of the amino acid sequence of a fragment of a Claudin-23 polypeptide, wherein the fragment consists of, in N-to-C order, a first transmembrane domain, a first extracellular loop, a second transmembrane domain, an intracellular loop, a third transmembrane domain, a second extracellular loop, and a fourth transmembrane domain of a Claudin-23 polypeptide of a Claudin-23 polypeptide. In such embodiments, each of the first and third transmembrane domains can be independently selected from the group consisting of amino acids 5 through 27 of SEQ ID NO:6 and amino acids 112 through 134 of SEQ ID NO:6, or the corresponding portions of SEQ ID NO:8, or variants thereof; and each of the second and fourth transmembrane domains can be independently selected from the group consisting of amino acids 77 through 99 of SEQ ID NO:6 and amino acids 160 through 182 of SEQ ID NO:6, or the corresponding portions of SEQ ID NO:8, or variants thereof.

The invention also provides an isolated polynucleotide selected from the group consisting of a polynucleotide comprising, consisting essentially of, or consisting of: (a) SEQ ID NO:5; (b) SEQ ID NO:5, wherein T can also be U; (c) a polynucleotide that encode an amino acid sequence as set forth in SEQ ID NO:6 or 8; (d) a fragment of (a), (b), or (c) that is at least 15 consecutive bases in length and that selectively hybridize to DNA which encodes a polypeptide of SEQ ID NO:6 or 8; and (e) a fragment of SEQ ID NO:5, wherein the fragment encodes a polypeptide having Claudin-23 polypeptide activity. In another aspect the invention provides an isolated polynucleotide that hybridizes under moderate to high stringency conditions to a polynucleotide consisting of a sequence as set forth in SEQ ID NO:5. In yet a further embodiment, the isolated polynucleotide comprises a Claudin-23 polynucleotide variant, wherein the variant shares nucleotide sequence identity with a nucleotide sequence as set forth by SEQ ID NO:5, wherein the percent nucleotide sequence identity is selected from the group consisting of: at least 90%, at least 95%, at least 97.5%, at least 99%, and at least 99.5%. In one embodiment, the polynucleotides of the invention consist essentially of specified portions of SEQ ID NO:5, or variants thereof, and do not comprise any of the polynucleotides disclosed in WO 02/099062, WO 03/008553, or WO 03/023013.

The invention also provides an expression vector comprising a polynucleotide of the invention, as well as a recombinant host cell transfected or transformed with the expression vector or a polynucleotide of the invention.

The invention further provides a process for producing a polypeptide, comprising culturing a recombinant host cell of the invention under conditions promoting expression of the polypeptide from the polynucleotide. In a further embodiment, the process further includes purifying said polypeptide.

The invention also provides a substantially purified antibody that binds to a polypeptide consisting of a sequence as set forth in SEQ ID NO:6 or 8. The antibody may be monoclonal, polyclonal, human, or humanized.

The invention provides a method of designing an inhibitor of a Claudin-23 polypeptide of the invention. The method includes determining a three-dimensional structure of the polypeptide, analyzing the three-dimensional structure for likely binding sites of a ligand or substrate, synthesizing a molecule is predicted to interact with the binding site, substrate, or ligand, and determining the polypeptide-inhibiting activity of the molecule.

The invention provides a method for identifying an agent that modulates Claudin-23 polypeptide activity comprising mixing a test agent with a Claudin-23 polypeptide and determining Claudin-23 polypeptide activity in the presence and absence of the test agent, wherein a difference in Claudin-23 polypeptide activity in the presence of the test agent relative to that in the absence of the test agent is indicative of an agent that modulates Claudin-23 polypeptide activity. In this manner both inhibitors (antagonists) and activators (agonists) of Claudin-23 polypeptide activity may be identified. In one embodiment of these methods of the invention, the determination of Claudin-23 polypeptide activity comprises an assessment of transcription and/or translation of skin differentiation markers such as, but not limited to, filaggrin, profilaggrin, involucrin, and keratin markers (such as K1, K2, K2e, K2p, K4, K5, K6, K8, K9, K10, K13, K14, K16, K17, K18, K19, and the like) by conventional techniques, for example the use of differentiation marker-specific probes.

In another aspect of the invention, a method is provided for identifying peptide agonists and antagonists of the cytokine polypeptides of the invention, the method comprising selecting at least one peptide that binds to a polypeptide of the invention, wherein the peptide is selected in a process comprising one or more techniques selected from yeast-based screening, rational design, protein structural analysis, screening of a phage display library, an *E. coli* display library, a ribosomal library, an RNA-peptide library, and a chemical peptide library. In further aspects of the invention, the peptide is selected from a plurality of randomized peptides.

Also provided by the invention is a method for increasing tight junction formation activity or epithelial or endothelial barrier function activity in a cell or subject comprising providing a Claudin-23 polypeptide of the invention, or an agonist thereof, to the cell or subject. In one embodiment of the invention, the agonist is an agonistic antibody or a peptide.

The invention further provides a method for decreasing tight junction formation activity or epithelial or endothelial barrier function activity in a cell or subject comprising providing an antagonist of a Claudin-23 polypeptide to the cell or subject. In one embodiment, the antagonist is an antibody or a soluble Claudin-23 domain.

The invention provides a method for treating an epithelial or endothelial barrier function condition in a subject comprising administering a Claudin-23 polypeptide, or an agonist thereof, to the subject. In one embodiment, the epithelial or endothelial barrier function condition is a disorder of cells derived from keratinocytes of the epithelium or of the hair follicle. In another embodiment, the epithelial or endothelial barrier function condition is selected from the group consisting of inflammation, asthma, allergy, metastasis of cancer cells, ion transport disorders such as magnesium transport defects in the kidney, psoriasis and other inflammatory dermatoses, hyperproliferative skin disorder, hair loss, and inflammatory bowel disease.

DETAILED DESCRIPTION OF THE INVENTION

The Claudin polypeptides are a related group of "tetraspan" polypeptides, polypeptides having four membrane-spanning or transmembrane domains that are associated with cellular tight junctions. Claudin family polypeptides are expressed in epithelial cells and/or endothelial cells throughout development, with individual members of the Claudin polypeptide family being expressed in different tissues. The physiological functions associated with a particular Claudin polypeptide are related to the functions performed by the particular tissue(s) in which it is expressed.

Because of their roles in tight junction formation, epithelial and endothelial barrier function, ion transport, and viral protein, enterotoxin, or allergen binding, Claudin polypeptides are associated with conditions involving unregulated or improperly regulated transport across the epithelium or endothelium such as inflammation, asthma, allergy, metastasis of cancer cells, and ion transport disorders such as magnesium transport defects in the kidney. In addition, because a Claudin polypeptide expressed in neural cells has been shown to be required for formation of the myelin sheath in oligodendrocytes, Claudin polypeptides are associated with demyelination conditions such as multiple sclerosis (MS), autoimmune encephalomyelitis, optic neuritis, progressive multifocal leukoencephalopathy (PML), and the like.

Characteristics and activities of the Claudin polypeptide family are described further in the following references:. Fujitaab K et al., 2000, Clostridium perfringens enterotoxin binds to the second extracellular loop of claudin-3, a tight junction integral membrane protein, FEBS Lett. 476: 258–261; Kinugasa T et al., 2000, Claudins regulate the intestinal barrier in response to immune mediators, Gastroenterology 118: 1001–1011; Tsukita S and Furuse M, 2000, Pores in the wall: claudins constitute tight junction strands containing aqueous pores, J Cell Biol. 149: 13–16; Bronstein J M et al., 2000, Involvement of OSP/claudin-11 in oligodendrocyte membrane interactions: role in biology and disease, J Neurosci Res. 59: 706–711; Itoh M et al., 1999, Direct binding of three tight junction-associated MAGUKs, ZO-1, ZO-2, and ZO-3, with the COOH termini of claudins, J Cell Biol. 147: 1351–1363; Furuse M et al., 1999, Manner of interaction of heterogeneous claudin species within and between tight junction strands, J Cell Biol. 147: 891–903; Morita K et al., 1999, Endothelial claudin: claudin-5/TM-VCF constitutes tight junction strands in endothelial cells, J Cell Biol. 147: 185–194; Kubota K et al., 1999, Ca(2+)-independent cell-adhesion activity of claudins, a family of integral membrane proteins localized at tight junctions, Curr Biol. 9: 1035–1038; Wan H et al., 1999, Der p 1 facilitates transepithelial allergen delivery by disruption of tight junctions, J Clin Invest. 104: 123–133; Simon D B et al., 1999, Paracellin-1, a renal tight junction protein required for paracellular $Mg^{2+}$ resorption, Science 285: 103–106; Morita K et at., 1999, Claudin multigene family encoding four-transmembrane domain protein components of tight junction strands, Proc Natl Acad Sci USA. 96: 511–516; Furuse M et al., 1998, A single gene product, claudin-1 or -2, reconstitutes tight junction strands and recruits occludin in fibroblasts, J Cell Biol. 143: 391–401; Furuse M et al., 1998, Claudin-1 and -2: novel integral membrane proteins localizing at tight junctions with no sequence similarity to occludin, J Cell Biol. 141: 1539–1550; all of which are incorporated by reference herein.

The invention provides polypeptides that are members of the Claudin polypeptide family, human Claudin-23 and murine Claudin-23. Typical structural elements common to members of the Claudin polypeptide family include a non-cleaved signal peptide sequence, four membrane-spanning domains, two extracellular loops formed by the membrane-spanning domains, and a cytoplasmic tail at the C-terminus of the polypeptide. Both the N-terminus and the C-terminus of the polypeptide are intracellular. The two extracellular loop domains of Claudin polypeptides are located between the first and second transmembrane domains and between the third and fourth transmembrane domains of the polypeptide, respectively. The extracellular loop domains of Claudin polypeptides may contribute to tight junction formation, which is an important aspect of both the barrier function and the ion transport function of Claudin polypeptides, and/or act as a receptor for viral proteins, enterotoxins, or allergens. The tight junction formation activities of the Claudin polypeptide family are believed to occur through homotypic interactions with the extracellular loops of the same Claudin polypeptide expressed on neighboring epithelial or endothelial cells, or heterotypic interactions with the extracellular loops of other Claudin family members or other non-Claudin polypeptides. In addition, there is evidence that the biological effects of Claudin polypeptides involve a requirement for Claudin polypeptides, and particularly their most N-terminal extracellular domain, in the processing of matrix metalloproteinases to their active form (Miyamori et al., 2001, *J Biol Chem* 276: 2804–28211). The short region between the second and third transmembrane domains of the polypeptide is intracellular. The cytoplasmic tail domain of Claudin polypeptides extends from the fourth transmembrane domain to the C-terminus of the polypeptide. The cytoplasmic tail domain is thought to be involved in interactions with other tight-junction-associated proteins such as the ZO (zona occludens) family of proteins. These interactive activities of Claudin polypeptides are thought to involve PDZ-domain-containing polypeptides, with a PDZ domain binding to the C-terminal residues of the cytoplasmic tail domain of a Claudin polypeptide; association of PDZ-containing polypeptides may then result in oligomerization of Claudin polypeptides.

The amino acid sequences of human Claudin-23 (SEQ ID NO:6) and murine Claudin-23 (SEQ ID NO:8) contain the structural features of Claudin polypeptides. Human Claudin-23 contains a first transmembrane (TM) domain from about amino acid 5 to about 27 of SEQ ID NO:6. Consistent with the other Claudin family members the first transmembrane domain is inserted into the cell membrane with the very N-terminal end of the Claudin polypeptide (in this case, including amino acids from about 1 to 4 of SEQ ID NO:6) located inside the cell. Human Claudin-23 is also predicted to have a second TM domain comprising from about amino acids 77 to 99 of SEQ ID NO:6, a third TM domain comprising from about amino acids 112 to 134 of SEQ ID NO:6, and a fourth TM domain comprising from about amino acids 160 to 182 of SEQ ID NO:6. Hidden Markov Model (HMM) analysis predicts similar transmembrane domains: from about amino acids 5 through 27 of SEQ ID NO:6; from about amino acids 78 through 100 of SEQ ID NO:6; from about amino acids 112 through 134 of SEQ ID NO:6; and from about amino acids 161 through 183 of SEQ ID NO:6. These predicted locations for the Human Claudin-23 TM domains also correspond well with those identified by Morita et al. (1999, Claudin multigene family encoding four-transmembrane domain protein components of tight junction strands, Proc Natl Acad Sci USA. 96: 511–516) for other members of the Claudin polypeptide family. Based on the alignments with other family members and by reference to FIG. 1 of Morita et al., the predicted locations for the four TM domains of Human Claudin-23 place the first extracellular loop of Human Claudin-23 as beginning approximately around amino acid 28 to amino acid 31 of SEQ ID NO:6 and extending to approximately amino acid 76 of SEQ ID NO:6, and the second extracellular loop of Human Claudin-23 as beginning approximately around amino acid 135 to amino acid 138 of SEQ ID NO:6 and extending to approximately amino acid 159 of SEQ ID NO:6. The intracellular sequence between the second and third TM domains begins at approximately amino acid 100 to 103 of SEQ ID NO:6 and extends to approximately amino acid 111 of SEQ ID NO:6. The cytoplasmic tail domain of Human Claudin-23 begins approximately around amino acid 182 to amino acid 184 (e.g., about amino acid 183) of SEQ ID NO:6 and extends to the predicted C-terminus of SEQ ID NO:6 at amino acid 292.

A Hidden Markov Model (HMM) analysis of murine Claudin-23 (SEQ ID NO:8) predicts the following transmembrane domains: from about amino acids 5 through 27 of SEQ ID NO:8; from about amino acids 79 through 101 of SEQ ID NO:8; from about amino acids 113 through 135 of SEQ ID NO:8; and amino acids 161 through 183 of SEQ ID NO:8. These predicted locations for the four TM domains of murine Claudin-23 place the first extracellular loop of murine Claudin-23 as beginning approximately around amino acid 28 to amino acid 31 of SEQ ID NO:8 and extending to approximately amino acid 78 of SEQ ID NO:8, and the second extracellular loop of murine Claudin-23 as beginning approximately around amino acid 136 to amino acid 138 of SEQ ID NO:8 and extending to approximately amino acid 160 of SEQ ID NO:8. The intracellular sequence between the second and third TM domains begins at approximately amino acid 102 to 105 of SEQ ID NO:8 and extends to approximately amino acid 112 of SEQ ID NO:8. The cytoplasmic tail domain of murine Claudin-23 begins approximately around amino acid 183 to amino acid 185 (e.g., about amino acid 184) of SEQ ID NO:8 and extends to the predicted C-terminus of SEQ ID NO:8 at amino acid 296.

The skilled artisan will recognize that the boundaries of these regions of these polypeptides are approximate and that the precise boundaries of such domains, as for example the boundaries of the transmembrane domains, may differ in 1–5 amino acids from those predicted herein for human and murine claudin-23.

The most C-terminal residues of the cytoplasmic tail domains of Claudin polypeptides are believed to be involved with interaction with PDZ-domain-containing proteins, such that substitutions of those residues are likely be associated with an altered PDZ domain recognition pattern or binding function, or with a lack of that function, for the polypeptide. Human Claudin-23 has an -Asp-Ser-Asp-Leu-COOH amino acid sequence at its C-terminus. Although this does not match exactly the C-terminal amino acid sequences of other Claudin family polypeptides, it is consistent in most respects with the consensus requirements for "Group 1" polypeptides that interact with PDZ domains (Cowburn D, 1997, *Curr Opin Struct Biol* 7: 835–838; which is incorporated by reference herein): Val/Ile/Leu/Met as the C-terminal residue, with preference for Thr/Ser/Tyr at the -2 position and Glu at the −3 position. Human Claudin-23 has Leu as the C-terminal residue and Asp, having an acidic side chain like Glu, at the −4 position. Human Claudin-23 may interact with PDZ-domain-containing polypeptides, although they may interact with different subsets of PDZ domains than other Claudin family members, or they may exhibit different kinetics or affinity in their interactions with PDZ-domain-containing polypeptides.

Biological Activities and Functions of Claudin Polypeptides of the Invention

As used herein, "Claudin polypeptides of the invention" includes human Claudin-23 (SEQ ID NO:6) and species homologues such as murine Claudin-23 (SEQ ID NO:8), and variants and fragments of these Claudin polypeptides and their species homologues. Claudin polypeptides of the invention have biological activities and functions that are consistent with those of the other Claudin family polypeptides. Polypeptides of the Claudin family are expressed in cell types including epithelial and endothelial cells throughout development. Typical biological activities or functions associated with this family of polypeptides are tight junction formation, epithelial or endothelial barrier function, ion transport, viral protein binding, homotypic or heterotypic binding, and binding PDZ domain binding. Polypeptides having tight junction formation activity bind to other tight-junction-associated molecules to form tight junction structures that regulate epithelial or endothelial barrier function and paracellular transport. The tight junction formation activity is associated with the extracellular loops and, at least under certain conditions, with the cytoplasmic tail domain of Claudin polypeptides. Thus, for uses requiring tight junction formation activity, human Claudin-23 polypeptides include those having the extracellular loop domains and exhibiting tight junction formation activities such as epithelial or endothelial barrier function, paracellular ion transport, or viral protein binding. Claudin polypeptides of the invention further include oligomers or fusion polypeptides comprising at least one extracellular loop or cytoplasmic tail domain of one or more Claudin polypeptides of the invention, and fragments of any of these polypeptides that have tight junction formation activity. The tight junction formation activity of human Claudin-23 and other Claudin family polypeptides may be determined, for example, by introducing Claudin polypeptides into cells that do not normally form tight junctions, such a L fibroblasts, along with occludin or any other polypeptide that the Claudin polypeptide needs to interact with in the formation of tight junctions, then visualizing the resulting tight junction structures by electron microscopy or immunofluorescence methods (see for example Furuse M et al., 1998, A single gene product, claudin-1 or -2, reconstitutes tight junction strands and recruits occludin in fibroblasts, J Cell Biol. 143: 391–401). Alternatively, the paracellular ion transport activity of human Claudin-23 and other Claudin family polypeptides may be assayed by electrophysiology or through the use of luminescent ion indicator molecules such as aequorin, preferably in micellular preparations from cells expressing Claudin polypeptides.

Claudin polypeptides such as human Claudin-23 have homotypic binding, heterotypic binding, viral protein binding, and/or enterotoxin binding activity; each of these binding activities is associated with the extracellular loop domains of Claudin polypeptides. Thus, for uses requiring homotypic binding, heterotypic binding, viral protein binding, and/or enterotoxin binding activity, Claudin polypeptides of the invention will include those having at least one extracellular loop domain and exhibiting at least one such binding activity. Claudin polypeptides also have PDZ domain-binding activity associated with the cytoplasmic tail domains of Claudin polypeptides. Thus, for uses requiring PDZ domain-binding activity, Claudin polypeptides of the invention will include those having a cytoplasmic tail domain and exhibiting PDZ domain-binding activity. Claudin polypeptides of the invention further include oligomers or fusion polypeptides comprising at least one extracellular loop domain and/or cytoplasmic tail domain of one or more Claudin polypeptides of the invention, and fragments of any of these polypeptides that have homotypic binding, heterotypic binding, viral protein binding, enterotoxin binding, and/or PDZ domain binding activity. The binding activity or activities of human Claudin-23 and species homologues and other Claudin family polypeptides may be determined, for example, in a yeast two-hybrid assay, or in an in vitro assay that measures binding between a Claudin polypeptide and one of its homotypic, heterotypic, viral protein, enterotoxin, and/or PDZ-domain-containing binding partners, where either the Claudin polypeptide or its binding partner is labeled with a radioactive, fluorescent, or bioluminescent protein such that binding can be detected.

The term "human Claudin polypeptide activity," as used herein, includes any one or more of the following: tight junction formation, epithelial or endothelial barrier function, and ion transport activity; homotypic binding, heterotypic binding, viral protein binding, enterotoxin binding, and PDZ domain binding activity; as well as the ex vivo and in vivo activities of Claudin polypeptides of the invention. The degree to which Claudin polypeptides of the invention and fragments and other derivatives of these polypeptides exhibit these activities can be determined by standard assay methods. Exemplary assays are disclosed herein; those of skill in the art will appreciate that other, similar types of assays can be used to measure the biological activities of Claudin polypeptides of the invention and other Claudin family members.

One aspect of the biological activity of Claudin polypeptides including human Claudin-23 is the ability of members of this polypeptide family to bind particular binding partners such homotypic and heterotypic polypeptides, viral proteins, enterotoxins, and PDZ-domain-containing polypeptides, with the extracellular loop domains binding, for example, to homotypic polypeptides, and the cytoplasmic tail domain binding to PDZ-domain-containing polypeptides. The term "binding partner," as used herein, includes ligands, receptors, substrates, antibodies, other Claudin polypeptides, the same human Claudin-23 polypeptide (in the case of homotypic interactions), and any other molecule that interacts with a human Claudin-23 polypeptide through contact or proximity between particular portions of the binding partner and the human Claudin-23 polypeptide. Binding partners for Claudin polypeptides of the invention are also expressed by epithelial and endothelial cells, as Claudin polypeptides expressed in epithelial cells bind to molecules on neighboring epithelial cells to form tight junctions, and Claudin polypeptides expressed in endothelial cells bind to molecules on neighboring endothelial cells. Therefore, the interactions between Claudin polypeptides of the invention and their binding partners are involved in mediating interactions between adjacent epithelial cells, and interactions between adjacent endothelial cells. Because the extracellular loop domains of Claudin polypeptides of the invention bind to homotypic or heterotypic polypeptides, a derivative polypeptide comprising one or more extracellular loop domains when expressed as a separate fragment from the rest of a human Claudin-23 polypeptide, or as a soluble polypeptide, fused for example to an immunoglobulin Fc domain, is expected to disrupt the binding of Claudin polypeptides of the invention to its binding partners. By binding to one or more binding partners, the separate extracellular loop domain(s) polypeptide likely prevents binding by the native human Claudin-23 polypeptide(s), and so acts in a dominant negative fashion to inhibit the biological activities mediated via binding of Claudin polypeptides of the invention to homotypic or heterotypic polypeptides. The biological activities and partner-binding properties of human Claudin-23 and other Claudin family polypeptides may be assayed by standard methods and by those assays described herein.

Polypeptides of the Claudin family such as human Claudin-23 are involved in epithelial or endothelial barrier function and transport diseases or conditions, that share as a common feature abnormal tight junction formation or improperly regulated tight junction function (i.e. abnormal epithelial or endothelial barrier function) in their etiology. More specifically, the following conditions involving epithelial or endothelial barrier function and/or binding to Claudin polypeptides are those that are known or are likely to involve the biological activities of Claudin polypeptides: inflammation (e.g., psoriasis and other inflammatory dermatoses), asthma, allergy, cell proliferative disorders (e.g., hyperproliferative skin disorders including skin cancer), metastasis of cancer cells, ion transport disorders such as magnesium transport defects in the kidney, inflammatory bowel disease, and exposure to Clostridium perfringens enterotoxin (CPE). In addition, because a Claudin polypeptide expressed in neural cells has been shown to be required for formation of the myelin sheath in oligodendrocytes, Claudin polypeptides are associated with demyelination conditions such as multiple sclerosis (MS), autoimmune encephalomyelitis, optic neuritis, and progressive multifocal leukoencephalopathy (PML). Also, diseases that are promoted by one or more of the conditions above may involve Claudin polypeptides, directly or indirectly. For example, susceptibility to sudden infant death syndrome (SIDS) has been associated with exposure to CPE. As described in Example 1 below, Claudin-23 has been shown to be down-regulated in mutant mice having defects of skin development, specifically differentation of keratinocyte-derived cells of the epithelium and the hair follicle. Therefore, Claudin-23 is involved in conditions and disorders affecting the skin epithelium and/or the hair follicle, for example conditions and disorders in which skin epithelial barrier function is abnormal or misregulated. Blocking or inhibiting the interactions between Claudin polypeptides of the invention and their substrates, ligands, receptors, binding partners, and or other interacting polypeptides is an aspect of the invention and provides methods for treating or ameliorating these diseases and conditions through the use of inhibitors of human Claudin-23 activity. Examples of such inhibitors or antagonists are described in more detail below. For certain conditions involving a defect in epithelial or endothelial barrier function or ion transport associated with too little human Claudin-23 activity, methods of treating or ameliorating these conditions comprise increasing the amount or activity of Claudin polypeptides of the invention by providing isolated Claudin polypeptides of the invention or active fragments or fusion polypeptides thereof, or by providing compounds (agonists) that activate endogenous or exogenous Claudin polypeptides of the invention. Additional uses for Claudin polypeptides of the invention and agonists and antagonists thereof include diagnostic reagents for epithelial or endothelial transport diseases; research reagents for investigation of occludin or ZO family polypeptides and the formation of tight junctions; purification, processing, and preservation of occludin or ZO polypeptides or of epithelial or endothelial cells; or as a carrier or targeting molecule for the delivery of therapeutic agents, particularly in view of the role of Claudins in the tight junctions of the blood-brain barrier (Kniesel U and Wolburg H. 2000, Cell Mol Neurobiol. 20: 57–76, which is incorporated by reference herein).

In one embodiment, a Claudin-23 polypeptide or polynucleotide plays a role as a tumor suppressor. For example, where there is a decrease in the amount or activity of Claudin-23 in a subject. the invention also provides methods of treating such a disorder characterized by a decrease in Claudin-23, and of preventing, reducing the risk of, ameliorating, or treating tumor formation or metastasis, comprising administering to the subject a therapeutically effective amount of a pharmaceutically acceptable solution containing an agonist of Claudin-23. The term "agonist," as used herein, refers to an agent that causes a change in Claudin-23 that increases a biological activity associated with Claudin-23. An agonist includes molecules that (1) increase the bioavailability of a Claudin-23 polypeptide, and/or (2) increase the expression of a Claudin-23 polynucleotide, and/or (3) simulate a biological activity of a Claudin-23 gene product. Such a molecule can include a polynucleotide, polypeptide, peptidomimetic, or small molecule. In one embodiment, a vector or cell comprising a recombinant polynucleotide encoding a Claudin-23 polypeptide is administered to the subject such that the polynucleotide is expressed thereby increasing the bioavailability of a Claudin-23 polypeptide. Such vectors may be administered to a subject in vivo through, for example, intravenous administration, or via ex vivo transfection of a subject's wherein the cells are infused into the subject. Such cells are typically homologous cells derived from tissue or serum of the subject, or they may include heterologous cells.

As demonstrated in the Examples below, Claudin-23 is found to be expressed in a number of inflammatory cells including dendritic cells and thus may play a role in inflammation as an immune system modulator. Accordingly, agonists and antagonists of Claudin-23 can be used to modulate the immune system.

Claudin Polypeptides of the Invention

A human Claudin-23 polypeptide is a polypeptide that (a) has a sequence as set forth in SEQ ID NO:6; (b) shares a sufficient degree of amino acid identity or similarity to a Claudin-23 polypeptide comprising an amino acid sequence as set forth in SEQ ID NO:6 or 7; (c) is identified by those of skill in the art as a polypeptide likely to share particular structural domains with a Claudin-23 polypeptide of SEQ ID NO:6 or 7; (d) has biological activities in common with a Claudin polypeptide; and/or (e) binds to antibodies that also specifically bind to a Claudin-23 polypeptide having a sequence as set forth in SEQ ID NO:6 or 7. Claudin polypeptides of the invention may be isolated from naturally occurring sources, or be recombinantly produced such that a recombinant Claudin polypeptide has the same structure as naturally occurring Claudin polypeptides, or may be produced to have structures that differ from naturally occurring Claudin polypeptides. Polypeptides derived from any human Claudin-23 polypeptide by any type of alteration (for example, but not limited to, insertions, deletions, or substitutions of, for example, 1–10 or more amino acids; changes in the state of glycosylation of the polypeptide; refolding or isomerization to change its three-dimensional structure or self-association state; and changes to its association with other polypeptides or molecules) are also Claudin polypeptides of the invention. Therefore, the polypeptides provided by the invention include polypeptides characterized by amino acid sequences similar to those of the Claudin polypeptides of the invention described herein, but into which modifications are naturally provided or deliberately engineered. A polypeptide that shares biological activities in common with Claudin polypeptides of the invention is a polypeptide having Claudin-23 activity. Examples of biological activities exhibited by members of the Claudin polypeptide family include, without limitation, tight junction formation, epithelial or endothelial barrier function, ion transport, homotypic or heterotypic binding, viral protein binding, and enterotoxin binding.

"An isolated polypeptide consisting essentially of an amino acid sequence" means that the polypeptide may have, in addition to said amino acid sequence, additional material covalently linked to either or both ends of the polypeptide, said additional material between 1 and 10,000 additional amino acids covalently linked to either end, each end, or both ends of polypeptide; or between 1 and 1,000 additional amino acids covalently linked to either end, each end, or both ends of the polypeptide; or between 1 and 100 additional amino acids covalently linked to either end, each end, or both ends of the polypeptide. Covalent linkage of additional amino acids to either end, each end, or both ends of the polypeptide according to the invention results in a novel combined amino acid sequence that is neither naturally occurring nor disclosed in the art.

The invention provides both full-length and mature forms of Claudin polypeptides of the invention. Full-length polypeptides are those having the complete primary amino acid sequence of the polypeptide as initially translated. The amino acid sequences of full-length polypeptides can be obtained, for example, by translation of the complete open reading frame ("ORF") of a cDNA molecule. Several full-length polypeptides may be encoded by a single genetic locus if multiple mRNA forms are produced from that locus by alternative splicing or by the use of multiple translation initiation sites. The "mature form" of a polypeptide refers to a polypeptide that has undergone post-translational processing steps such as cleavage of the signal sequence or proteolytic cleavage to remove a prodomain. Multiple mature forms of a particular full-length polypeptide may be produced, for example by cleavage of the signal sequence at multiple sites, or by differential regulation of proteases that cleave the polypeptide. The mature form(s) of such polypeptide may be obtained by expression, in a suitable mammalian cell or other host cell, of a polynucleotide molecule that encodes the full-length polypeptide. The sequence of the mature form of the polypeptide may also be determinable from the amino acid sequence of the full-length form, through identification of signal sequences or protease cleavage sites. The Claudin polypeptides of the invention also include those that result from post-transcriptional or post-translational processing events such as alternate mRNA processing which can yield a truncated but biologically active polypeptide, for example, a naturally occurring soluble form of the polypeptide. Also encompassed within the invention are variations attributable to proteolysis such as differences in the N- or C-termini upon expression in different types of host cells, due to proteolytic removal of one or more terminal amino acids from the polypeptide (generally from 1 to 5 terminal amino acids).

The invention further includes Claudin polypeptides of the invention with or without associated native-pattern glycosylation. Polypeptides expressed in yeast or mammalian expression systems (e.g., COS-1 or CHO cells) can be similar to or significantly different from a native polypeptide in molecular weight and glycosylation pattern, depending upon the choice of expression system. Expression of polypeptides of the invention in bacterial expression systems, such as E. coli, provides non-glycosylated molecules. Further, a given preparation can include multiple differentially glycosylated species of the polypeptide. Glycosyl groups can be removed through conventional methods, in particular those utilizing glycopeptidase. In general, glycosylated polypeptides of the invention can be incubated with a molar excess of glycopeptidase (Boehringer Mannheim).

Species homologues of Claudin polypeptides of the invention (e.g., the Claudin-23 human and murine forms) and of polynucleotides encoding them are also provided by the invention. As used herein, a "species homologue" is a polypeptide or polynucleotide with a different species of origin from that of a given polypeptide or polynucleotide, but with significant sequence similarity to the given polypeptide or polynucleotide, as determined by those of skill in the art. Species homologues may be isolated and identified by making suitable probes or primers from polynucleotides encoding the amino acid sequences provided herein and screening a suitable nucleic acid source from the desired species. The invention also encompasses allelic variants of Claudin polypeptides of the invention and polynucleotides encoding them; that is, naturally-occurring alternative forms of such polypeptides and polynucleotides in which differences in amino acid or nucleotide sequence are attributable to genetic polymorphism (allelic variation among individuals within a population).

Fragments of the Claudin polypeptides of the invention may be in linear form or cyclized using known methods, for example, as described in H. U. Saragovi, et al., Bio/Technology 10, 773–778 (1992) and in R. S. McDowell, et al., J. Amer. Chem. Soc. 114 9245–9253 (1992), both of which are incorporated by reference herein. Polypeptides and polypeptide fragments of the invention, and polynucleotides encoding them, include polypeptides and polynucleotides with amino acid or nucleotide sequence lengths that are at least 25% (e.g., at least 50%, or at least 60%, or at least 70%, or at least 80%) of the length of a Claudin-23 polypeptide and have at least 60% sequence identity (e.g., at least 70%, at least 75%, at least 80%, at least 85%, at least 90%, at least 95%, at least 97.5%, or a 99%, or at least 99.5%) with a Claudin-23 polypeptide or encoding polynucleotide, where sequence identity is determined by comparing the amino acid sequences of the polypeptides when aligned so as to maximize overlap and identity while minimizing sequence gaps. Also included in the invention are polypeptides and polypeptide fragments, and polynucleotides encoding them, that contain or encode a segment typically comprising at least 8, or at least 10, or at least 15, or at least 20, or at least 30, or at least 40 contiguous amino acids. Such polypeptides and polypeptide fragments may also contain a segment that shares at least 70% sequence identity (or at least 70%, at least 75%, at least 80%, at least 85%, at least 90%, at least 95%, at least 97.5%, at least 99%, or at least 99.5%) with any such segment of any of the Claudin polypeptides of the invention, where sequence identity is determined by comparing the amino acid sequences of the polypeptides when aligned so as to maximize overlap and identity while minimizing sequence gaps. The percent identity can be determined by visual inspection and mathematical calculation. Alternatively, the percent identity of two amino acid or two polynucleotide sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The typical default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds.,

*Atlas of Polypeptide Sequence and Structure*, National Biomedical Research Foundation, pp. 353–358, 1979; (2) a penalty of 3.0 for each gap and an additional 0.10 penalty for each symbol in each gap; and (3) no penalty for end gaps. Other programs used by those skilled in the art of sequence comparison may also be used, such as, for example, the BLASTN program version 2.0.9, available for use via the National Library of Medicine website ncbi.nlm.nih.gov/gorf/wblast2.cgi, or the UW-BLAST 2.0 algorithm. Standard default parameter settings for UW-BLAST 2.0 are described at the following Internet webpage: blast.wustl.edu/blast/README.html#References. In addition, the BLAST algorithm uses the BLOSUM64 amino acid scoring matrix, and optional parameters that may be used are as follows: (A) inclusion of a filter to mask segments of the query sequence that have low compositional complexity (as determined by the SEG program of Wootton & Federhen (Computers and Chemistry, 1993); also see Wootton J C and Federhen S. 1996, Analysis of compositionally biased regions in sequence databases, *Methods Enzymol.* 266: 554–71) or segments consisting of short-periodicity internal repeats (as determined by the XNU program of Claverie & States (Computers and Chemistry, 1993)), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); typical E-score threshold values are 0.5, or 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The invention also provides for soluble forms of Claudin polypeptides of the invention comprising certain fragments or domains of these polypeptides, and particularly those comprising the extracellular domain or one or more fragments of the extracellular domain. Soluble polypeptides are polypeptides that are capable of being secreted from the cells in which they are expressed. In such forms part or all of the intracellular and transmembrane domains of the polypeptide are deleted such that the polypeptide is fully secreted from the cell in which it is expressed. The intracellular and transmembrane domains of polypeptides of the invention can be identified in accordance with known techniques for determination of such domains from sequence information. Soluble Claudin polypeptides of the invention also include those polypeptides which include part of the transmembrane region, provided that the soluble Claudin-23 polypeptide is capable of being secreted from a cell, and which typically retains a human Claudin-23 activity. Soluble Claudin polypeptides of the invention further include oligomers or fusion polypeptides comprising the extracellular portion of at least one Claudin-23 polypeptide, and fragments that have Claudin-23 activity. A secreted soluble polypeptide may be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. The use of soluble forms of Claudin polypeptides of the invention is advantageous for many applications. Purification of the polypeptides from recombinant host cells is facilitated, since the soluble polypeptides are secreted from the cells. Moreover, soluble polypeptides are generally more suitable than membrane-bound forms for parenteral administration and for many enzymatic procedures.

In another aspect of the invention, polypeptides comprise various combinations of Claudin-23 polypeptide domains, such as the cytoplasmic tail domain and the extracellular loop domain or a cytoplasmic tail and a cytoplasmic loop domain. Accordingly, polypeptides of the invention and polynucleotides encoding them include those comprising or encoding two or more copies of a domain such as the cytoplasmic tail domain, two or more copies of a domain such as the extracellular loop domain, or at least one copy of each domain, and these domains may be presented in any order within such polypeptides.

Further modifications in the peptide or DNA sequences can be made by those skilled in the art using known techniques. Modifications of interest in the polypeptide sequences may include the alteration, substitution, replacement, insertion or deletion of a selected amino acid. For example, one or more of the cysteine residues may be deleted or replaced with another amino acid to alter the conformation of the molecule, an alteration which may involve preventing formation of incorrect intramolecular disulfide bridges upon folding or renaturation. Techniques for such alteration, substitution, replacement, insertion or deletion are well known to those skilled in the art (see, e.g., U.S. Pat. No. 4,518,584). As another example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in polypeptides include those described in U.S. Pat. Nos. 5,071,972 and EP 276,846, hereby incorporated by reference. Additional variants within the scope of the invention include polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Conjugates comprising diagnostic (detectable) or therapeutic agents attached thereto are contemplated herein. Preferably, such alteration, substitution, replacement, insertion or deletion retains the desired activity of the polypeptide or a substantial equivalent thereof. One example is a variant that binds with essentially the same binding affinity as does the native form. Binding affinity can be measured by conventional procedures, e.g., as described in U.S. Pat. No. 5,512,457 and as set forth herein.

Other derivatives include covalent or aggregative conjugates of the polypeptides with other polypeptides or polypeptides, such as by synthesis in recombinant culture as N-terminal or C-terminal fusions. Examples of fusion polypeptides are discussed below in connection with oligomers. Further, fusion polypeptides can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, which is highly antigenic and provides an epitope reversibly bound by a specific monoclonal antibody, enabling rapid assay And facile purification of expressed recombinant polypeptide. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Encompassed by the invention are oligomers or fusion polypeptides that contain a Claudin-23 polypeptide, one or more fragments of Claudin polypeptides of the invention, or any of the derivative or variant forms of Claudin polypeptides of the invention as disclosed herein. In particular embodiments, the oligomers comprise soluble Claudin polypeptides of the invention. Oligomers can be in the form of covalently linked or non-covalently-linked multimers, including dimers, trimers, or higher oligomers. In one aspect of the invention, the oligomers maintain the binding ability of the polypeptide components and provide therefor, bivalent, trivalent, etc., binding sites. In an alternative embodiment the invention is directed to oligomers comprising multiple Claudin polypeptides of the invention joined via covalent or non-covalent interactions between peptide moieties fused to the polypeptides, such peptides having the property of promoting oligomerization. Leucine zippers and certain polypeptides derived from antibodies are among the peptides that can promote oligomerization of the polypeptides attached thereto, as described in more detail below.

In embodiments where variants of the Claudin polypeptides of the invention are constructed to include a membrane-spanning domain, they will form a membrane-spanning polypeptide. Membrane-spanning Claudin polypeptides of the invention can be fused with extracellular domains of receptor polypeptides for which the ligand is known. Such fusion polypeptides can then be manipulated to control the intracellular signaling pathways triggered by the membrane-spanning Claudin-23 polypeptide. Claudin polypeptides of the invention that span the cell membrane can also be fused with agonists or antagonists of cell-surface receptors, or cellular adhesion molecules to further modulate Claudin-23 intracellular effects. In another aspect of the invention, interleukins can be situated between Claudin-23 polypeptide fragment and other fusion polypeptide domains.

Immunoglobulin-based Oligomers. The polypeptides of the invention or fragments thereof may be fused to molecules such as immunoglobulins for many purposes, including increasing the valency of polypeptide binding sites. For example, fragments of a Claudin-23 polypeptide may be (a) fused directly or through a linker peptide to the Fc portion of an immunoglobulin, or (b) fused directly or through a linker peptide to another Claudin-23 polypeptide. For a bivalent form of the polypeptide, such a fusion could be to the Fc portion of an IgG molecule. Other immunoglobulin isotypes may also be used to generate such fusions. For example, a polypeptide-IgM fusion would generate a decavalent form of the polypeptide of the invention. The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Useful Fc polypeptides comprise an Fc polypeptide derived from a human IgG1 antibody. As one alternative, an oligomer is prepared using polypeptides derived from immunoglobulins. Preparation of fusion polypeptides comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Polypeptides", in *Current Protocols in Immunology*, Suppl. 4, pages 10.19.1–10.19.11, 1992). Methods for preparation and use of immunoglobulin-based oligomers are well known in the art. One embodiment of the invention is directed to a dimer comprising two fusion polypeptides created by fusing a polypeptide of the invention to an Fc polypeptide derived from an antibody. A gene fusion encoding the polypeptide/Fc fusion polypeptide is inserted into an appropriate expression vector. Polypeptide/Fc fusion polypeptides are expressed in host cells transformed with the recombinant expression vector, and allowed to assemble much like antibody molecules, whereupon interchain disulfide bonds form between the Fc moieties to yield divalent molecules. One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fe mutein described in U.S. Pat. No. 5,457,035 and in Baum et al., (*EMBO J.* 13:3992–4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fe receptors. The above-described fusion polypeptides comprising Fe moieties (and oligomers formed therefrom) offer the advantage of facile purification by affinity chromatography over Polypeptide A or Polypeptide G columns. In other embodiments, the polypeptides of the invention can be substituted for the variable portion of an antibody heavy or light chain. If fusion polypeptides are made with both heavy and light chains of an antibody, it is possible to form an oligomer with as many as four Claudin-23 extracellular regions.

Peptide-linker Based Oligomers. Alternatively, the oligomer is a fusion polypeptide comprising multiple Claudin polypeptides of the invention, with or without peptide linkers (spacer peptides). Among the suitable peptide linkers are those described in U.S. Pat. Nos. 4,751,180 and 4,935,233, which are hereby incorporated by reference. An oligonucleotide sequence encoding a desired peptide linker can be inserted between, and in the same reading frame as a Claudin polynucleotide of the invention, using any suitable conventional technique. For example, a chemically synthesized oligonucleotide encoding a peptide linker can be ligated between the sequences. In particular embodiments, a fusion polypeptide comprises from two to four soluble Claudin polypeptides of the invention, separated by peptide linkers. Suitable peptide linkers, their combination with other polypeptides, and their use are well known by those skilled in the art Leucine-Zippers. Another method for preparing the oligomers of the invention involves use of a leucine zipper. Leucine zipper domains are peptides that promote oligomerization of the polypeptides in which they are found. Leucine zippers were originally identified in several DNA-binding polypeptides (Landschulz et al., *Science* 240:1759, 1988), and have since been found in a variety of different polypeptides. Among the known leucine zippers are naturally occurring peptides and derivatives thereof that dimerize or trimerize. The zipper domain (also referred to herein as an oligomerizing, or oligomer-forming, domain) comprises a repetitive heptad repeat, often with four or five leucine residues interspersed with other amino acids. Use of leucine zippers and preparation of oligomers using leucine zippers are well known in the art.

Other fragments and derivatives of the sequences of polypeptides which would be expected to retain polypeptide activity in whole or in part and may thus be useful for screening or other immunological methodologies may also be made by those skilled in the art given the disclosures herein. Such modifications are encompassed by the invention.

Polynucleotides Encoding Claudin Polypeptides of the Invention

Encompassed within the invention are polynucleotides encoding Claudin polypeptides of the invention. These polynucleotides can be identified in several ways, including isolation of genomic or cDNA molecules from a suitable source. Nucleotide sequences corresponding to the amino acid sequences described herein, to be used as probes or primers for the isolation of polynucleotides or as query sequences for database searches, can be obtained by "back-translation" from the amino acid sequences, or by identification of regions of amino acid identity with polypeptides for which the coding DNA sequence has been identified. The well-known polymerase chain reaction (PCR) procedure can be employed to isolate and amplify a DNA sequence encoding a human Claudin-23 polypeptide or a desired combination of human Claudin-23 polypeptide fragments. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., *Science* 239:487 (1988); *Recombinant DNA Methodology*, Wu et al., eds., Academic. Press, Inc., San Diego (1989), pp. 189–196; and *PCR Protocols: A Guide to Methods and Applications*, Innis et al., eds., Academic Press, Inc. (1990).

Polynucleotide molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The polynucleotide molecules of the invention include full-length genes or cDNA molecules as well as a combination of fragments thereof. The polynucleotides of the invention can be derived from human sources, but the invention includes those derived from non-human species, as well.

"An isolated polynucleotide consisting essentially of a Claudin-23 polynucleotide" means that the polynucleotide may have, in addition to a specified Claudin-23 polynucleotide, additional material covalently linked to either or both ends of the polynucleotide molecule, said additional material being in one embodiment between 1 and 100,000 additional nucleotides; or between 1 and 10,000 additional nucleotides covalently linked to either end, each end, or both ends of the polynucleotide molecule; or between 10 and 1,000 additional nucleotides covalently linked to either end, each end, or both ends of the polynucleotide molecule; wherein the Claudin-23 polynucleotide encodes a Claudin-23 polypeptide or a fragment or variant thereof. An isolated polynucleotide consisting essentially of a Claudin-23 polynucleotide may be an expression vector or other construct comprising said Claudin-23 polynucleotide.

An "isolated polynucleotide" is a polynucleotide that has been separated from adjacent genetic sequences present in the genome of the organism from which the polynucleotide was isolated, in the case of polynucleotides isolated from naturally occurring sources. In the case of polynucleotides synthesized enzymatically from a template or chemically, such as PCR products, cDNA molecules, or oligonucleotides for example, it is understood that the polynucleotides resulting from such processes are isolated polynucleotides. An isolated polynucleotide refers to a polynucleotide in the form of a separate fragment or as a component of a larger polynucleotide construct. In one embodiment, the invention relates to certain isolated polynucleotides that are substantially free from contaminating endogenous material. The polynucleotide has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual*, 2nd ed., Cold Spring Harbor Laboratory, Cold Spring Harbor, N.Y. (1989)). Such sequences are typically provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The invention also includes polynucleotides that hybridize under moderately stringent conditions, or under highly stringent conditions, to polynucleotides encoding Claudin polypeptides of the invention. The basic parameters affecting the choice of hybridization conditions and guidance for devising suitable conditions are set forth by Sambrook, et al. (1989, Molecular Cloning: A Laboratory Manual, Cold Spring Harbor Laboratory Press, Cold Spring Harbor, N.Y., chapters 9 and 11; and Current Protocols in Molecular Biology, 1995, F. M. Ausubel et al., eds., John Wiley & Sons, Inc., sections 2.10 and 6.3–6.4, incorporated herein by reference), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5×SSC, 0.1% SDS. Generally, highly stringent conditions are defined as hybridization conditions as above, but with washing at approximately 68degrees C., 0.2×SSC, 0.1% SDS. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10 degrees C. less than the melting temperature ($T_m$) of the hybrid, where $T_m$ is determined according to the following equations. For hybrids less than 18 base pairs in length, $T_m$ (degrees C.)=2(# of A+T bases)+4(# of #G+C bases). For hybrids above 18 base pairs in length, $T_m$ (degrees C.)=81.5+16.6($\log_{10}$ [$Na^+$])+0.41(% G+C)−(600/N), where N is the number of bases in the hybrid, and [$Na^+$] is the concentration of sodium ions in the hybridization buffer ([$Na^+$] for 1×SSC=0.165M). Typically, each such hybridizing polynucleotide has a length that is at least 15, 18, 20, 25, 30, 40, or more typically 50 nucleotides, or at least 25% (e.g., at least 50%, or at least 60%, or at least 70%, or at least 80%) of the length of the polynucleotide of the invention to which it hybridizes, and has at least 60% sequence identity (e.g., at least 70%, at least 75%, at least 80%, at least 85%, at least 90%, at least 95%, at least 97.5%, at least 99%, or at leas 99.5%) with the polynucleotide of the invention to which it hybridizes, where sequence identity is determined by comparing the sequences of the hybridizing nucleic acids when aligned so as to maximize overlap and identity while minimizing sequence gaps as described in more detail above.

The invention also provides genes corresponding to the polynucleotide sequences disclosed herein. "Corresponding genes" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

Methods for Making and Purifying Claudin Polypeptides of the Invention

Methods for making Claudin polypeptides of the invention are described below. Expression, isolation, and purification of the polypeptides and fragments of the invention can be accomplished by any suitable technique, including but not limited to the following methods. The isolated nucleic acid of the invention can be operably linked to an expression control sequence such as the pDC409 vector (Giri et al., 1990, *EMBO J.* 13: 2821) or the derivative pDC412 vector (Wiley et al., 1995, *Immunity* 3: 673). The pDC400 series vectors are useful for transient mammalian expression systems, such as CV-1 or 293 cells. Alternatively, the isolated nucleic acid of the invention can be linked to expression vectors such as pDC312, pDC316, or pDC317 vectors. The pDC300 series vectors all contain the SV40 origin of replication, the CMV promoter, the adenovirus tripartite leader, and the SV40 polyA and termination signals, and are useful for stable mammalian expression systems, such as CHO cells or their derivatives. Other expression control sequences and cloning technologies can also be used to produce the polypeptide recombinantly, such as the pMT2 or pED expression vectors (Kaufman et al., 1991, *Nucleic Acids Res* 19: 4485–4490; and Pouwels et al., 1985, *Cloning Vectors: A Laboratory Manual,* Elsevier, N.Y.) and the GATEWAY Vectors (Life Technologies; Rockville, Md.). The isolated nucleic acid of the invention, flanked by attB sequences, can be recombined through an integrase reaction with a GATEWAY vector such as pDONR201 containing attP sequences, providing an entry vector for the GATEWAY system containing the isolated nucleic acid of the invention. This entry vector can be further recombined with other suitably prepared expression control sequences, such as those of the pDC400 and pDC300 series described above. Many suitable expression control sequences are known in the art. General methods of expressing recombinant polypeptides are also described in Kaufman, 1990, *Methods in Enzymology* 185, 537–566. As used herein "operably linked" means that a polynucleotide of the invention and an expression control sequence are situated within a construct, vector, or cell in such a way that a polypeptide encoded by a polynucleotide is expressed when appropriate molecules (such as polymerases) are present. As one embodiment of the invention, at least one expression control sequence is operably linked to a polynucleotide of the invention in a recombinant host cell or progeny thereof, the polynucleotide and/or expression control sequence having been introduced into the host cell by transformation or transfection, for example, or by any other suitable method. As another embodiment of the invention, at least one expression control sequence is integrated into the genome of a recombinant host cell such that it is operably linked to a polynucleotide sequence encoding a polypeptide of the invention. In a further embodiment of the invention, at least one expression control sequence is operably linked to a polynucleotide of the invention through the action of a trans-acting factor such as a transcription factor, either in vitro or in a recombinant host cell.

In addition, a sequence encoding an appropriate signal peptide (native or heterologous) can be incorporated into expression vectors. The choice of signal peptide or leader can depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846. A DNA sequence for a signal peptide (secretory leader) can be fused in frame to a polynucleotide of the invention so that the DNA is initially transcribed, and the mRNA translated, into a fusion polypeptide comprising the signal peptide. A signal peptide that is functional in the intended host cells promotes extracellular secretion of the polypeptide. The signal peptide is cleaved from the polypeptide upon secretion of polypeptide from the cell. The skilled artisan will also recognize that the position(s) at which the signal peptide is cleaved can differ from that predicted by computer program, and can vary according to such factors as the type of host cells employed in expressing a recombinant polypeptide. A polypeptide preparation can include a mixture of polypeptide molecules having different N-terminal amino acids, resulting from cleavage of the signal peptide at more than one site.

Established methods for introducing DNA into mammalian cells have been described (Kaufman, 1990, *Large Scale Mammalian Cell Culture*, pp. 15–69). Additional protocols using commercially available reagents, such as Lipofectamine lipid reagent (Gibco/BRL) or Lipofectamine-Plus lipid reagent, can be used to transfect cells (Felgner et al., 1987, *Proc. Natl. Acad Sci. USA* 84:7413–7417). In addition, electroporation can be used to transfect mammalian cells using conventional procedures, such as those in Sambrook et al., (*Molecular Cloning: A Laboratory Manual*, 2 ed. Vol. 1–3, Cold Spring Harbor Laboratory Press, 1989). Selection of stable transformants can be performed using methods known in the art such as, for example, resistance to cytotoxic drugs. Kaufman et al., *Meth. in Enzymology* 185:487–511, 1990, describes several selection schemes, such as dihydrofolate reductase (DHFR) resistance. A suitable strain for DHFR selection can be CHO strain DX-B11, which is deficient in DHFR (Urlaub and Chasin, *Proc. Natl. Acad. Sci. USA* 77:4216–4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Alternatively, gene products can be obtained via homologous recombination, or "gene targeting," techniques. Such techniques employ the introduction of exogenous transcription control elements (such as the CMV promoter or the like) in a particular predetermined site on the genome, to induce expression of the endogenous polynucleotide sequence of interest. The location of integration into a host chromosome or genome can be easily determined by one of skill in the art, given the known location and sequence of the gene. In one embodiment, the invention also contemplates the introduction of exogenous transcriptional control elements in conjunction with an amplifiable gene, to produce increased amounts of the gene product, again, without the need for isolation of the gene itself from the host cell. The practice of homologous recombination or gene targeting is explained by Schimke, et al." *Amplification of Genes in Somatic Mammalian cells,"* Methods in Enzymology 151:85–104 (1987), as well as by Capecchi, et al., "*The New Mouse Genetics: Altering the Genome by Gene Targeting,"* TIG 5:70–76 (1989).

A number of types of cells may act as suitable host cells for expression of a polypeptide. Mammalian host cells include, for example, the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, BHK (ATCC CRL 10) cell lines, the CV1/EBNA cell line derived from the African green monkey kidney cell line CV1 (ATCC CCL 70) as described by McMahan et al. (*EMBO J.* 10:2821, 1991), human kidney 293 cells, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, it may be possible to produce a polypeptide in lower eukaryotes such as yeast or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous polypeptides. Potentially suitable bacterial strains include *Eseherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain the functional polypeptide. Such covalent attachments may be accomplished using known chemical or enzymatic methods. The polypeptide may also be produced by operably linking an isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MAXBAC® Baculovirus expression system), and such methods are well known in the art, as described in Summers and Smith, Texas Agricultural Experiment Station Bulletin No. 1555 (1987), and Luckow and Summers, *Bio/Technology* 6:47 (1988), incorporated herein by reference. As used herein, an insect cell capable of expressing a polynucleotide of the invention is "transformed." Cell-free translation systems could also be employed to produce polypeptides using RNAs derived from polynucleotide constructs disclosed herein. A host cell that comprises an isolated polynucleotide of the invention, typically operably linked to at least one expression control sequence, is a "recombinant host cell".

A polypeptide of the invention may be prepared by culturing transformed host cells under culture conditions suitable to express the recombinant polypeptide. The resulting expressed polypeptide may then be purified from such culture (e.g., from culture medium or cell extracts) using known purification processes, such as gel filtration and ion exchange chromatography. The purification of a polypeptide may also include an affinity column containing agents which will bind to the polypeptide; one or more colunm steps over such affinity resins as concanavalin A-agarose, HEPARIN-TOYOPEARL® (hydrophilic polymer gel) or Cibacrom blue 3GA SEPHAROSE® (agarose beads); one or more steps involving hydrophobic interaction chromatography using such resins as phenyl ether, butyl ether, or propyl ether; or immunoaffinity chromatography. Alternatively, a polypeptide of the invention may also be expressed in a form that will facilitate purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. A polypeptide can also be tagged with an epitope and subsequently purified by using a specific antibody directed to such epitope. One such epitope ("Flag") is commercially available from Kodak (New Haven, Conn.). Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous isolated recombinant polypeptide. A polypeptide thus purified is substantially free of other mammalian polypeptides and is defined in accordance with the invention as a "purified polypeptide"; such purified polypeptides of the invention include purified antibodies that bind to Claudin polypeptides of the invention, fragments, variants, binding partner, and the like. A polypeptide of the invention may also be expressed as a product of transgenic animals, e.g., as a component of the milk of transgenic cows, goats, pigs, or sheep which are characterized by somatic or germ cells containing a polynucleotide encoding the polypeptide.

It is also possible to utilize an affinity column comprising a polypeptide-binding polypeptide of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention. In this aspect of the invention, polypeptide-binding polypeptides, such as the anti-polypeptide antibodies of the invention or other polypeptides that can interact with a polypeptide of the invention, can be bound to a solid phase support such as a column chromatography matrix or a similar substrate suitable for identifying, separating, or purifying cells that express polypeptides of the invention on their surface. Adherence of polypeptide-binding polypeptides of the invention to a solid phase contacting surface can be accomplished by any number of techniques, for example, magnetic microspheres can be coated with these polypeptide-binding polypeptides and held in the incubation vessel through a magnetic field. Suspensions of cell mixtures are contacted with the solid phase that has such polypeptide-binding polypeptides thereon. Cells having polypeptides of the invention on their surface bind to the fixed polypeptide-binding polypeptide and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are directed to cleaving the cell-surface binding partner. Alternatively, mixtures of cells suspected of containing .polypeptide-expressing cells of the invention can first be incubated with a biotinylated polypeptide-binding polypeptide of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art (see, e.g., Berenson, et al. *J. Cell. Biochem.*, 10D:239, 1986). Wash of unbound material and the release of the bound cells is performed using conventional methods A polypeptide may also be produced by known conventional chemical synthesis. Methods for constructing polypeptides of the invention by synthetic means are known to those skilled in the art. The synthetically constructed polypeptides, by virtue of sharing primary, secondary or tertiary structural and/or conformational characteristics with native polypeptides may possess biological properties in common therewith, including polypeptide activity. Thus, they may be employed as biologically active or immunological substitutes for natural, purified polypeptides in screening of therapeutic compounds and in immunological processes for the development of antibodies.

The desired degree of purity depends on the intended use of a polypeptide. A relatively high degree of purity is desired when a polypeptide is to be administered in vivo, for example. In such a case, polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. A polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

Antagonists and Agonists of Claudin Polypeptides of the Invention

Any method that neutralizes Claudin polypeptides of the invention or inhibits expression of a Claudin-23 gene (either transcription or translation) can be used to reduce the biological activities of Claudin polypeptides of the invention. In particular embodiments, antagonists inhibit the binding of at least one Claudin-23 polypeptide to binding partners expressed on cells, thereby inhibiting biological activities induced by the binding of those Claudin polypeptides of the invention to the cells. In certain other embodiments of the invention, antagonists can be designed to reduce the level of endogenous Claudin-23 gene expression, e.g., using well-known antisense or ribozyme approaches to inhibit or prevent translation of Claudin-23 mRNA transcripts; triple helix approaches to inhibit transcription of Claudin-23 genes; or targeted homologous recombination to inactivate or "knock out" a Claudin-23 gene or their endogenous promoters or enhancer elements. Such antisense, ribozyme, and triple helix antagonists may be designed to reduce or inhibit either unimpaired, or if appropriate, mutant Claudin-23 gene activity. Techniques for the production and use of such molecules are well known to those of skill in the art.

Antisense RNA and DNA molecules act to directly block the translation of mRNA by hybridizing to targeted mRNA and preventing polypeptide translation. Antisense approaches involve the design of oligonucleotides (either DNA or RNA) that are complementary to a Claudin-23 mRNA. The antisense oligonucleotides will bind to the complementary target gene mRNA transcripts and prevent translation. Absolute complementarity, although preferred, is not required. A sequence "complementary" to a portion of a polynucleotide, as referred to herein, means a sequence having sufficient complementarity to be able to hybridize with the polynucleotide, forming a stable duplex (or triplex, as appropriate). In the case of double-stranded antisense nucleic acids, a single strand of the duplex DNA may thus be tested, or triplex formation may be assayed. The ability to hybridize will depend on both the degree of complementarity and the length of the antisense nucleic acid. Oligonucleotides that are complementary to the 5' end of the message, e.g., the 5' untranslated sequence up to and including the AUG initiation codon, should work most efficiently at inhibiting translation. However, oligonucleotides complementary to either the 5'- or 3'- non-translated, non-coding regions of a Claudin-23 gene transcript could be used in an antisense approach to inhibit translation of endogenous Claudin-23 mRNA. Oligonucleotides complementary to the 5' untranslated region of the mRNA should include the complement of the AUG start codon. Antisense nucleic acids should be at least six nucleotides in length, and typically range from 6 to about 50 nucleotides in length. In specific aspects the oligonucleotide is at least 10 nucleotides at least 17 nucleotides, at least 25 nucleotides or at least 50 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, and the like. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988), or hybridization-triggered cleavage agents or intercalating agents (see, e.g., Zon, 1988, Pharm. Res. 5:539–549). The antisense molecules should be delivered to cells that express a human Claudin-23 transcript in vivo. A number of methods have been developed for delivering antisense DNA or RNA to cells; e.g., antisense molecules can be injected directly into the tissue or cell derivation site, or modified antisense molecules, designed to target the desired cells (e.g., antisense linked to peptides or antibodies that specifically bind receptors or antigens expressed on the target cell surface) can be administered systemically. However, it is often difficult to achieve intracellular concentrations of the antisense molecule sufficient to suppress translation of endogenous mRNAs. Therefore one approach utilizes a recombinant DNA construct in which the antisense oligonucleotide is placed under the control of a strong pol III or pol II promoter. The use of such a construct to transfect target cells in a subject will result in the transcription of sufficient amounts of single stranded RNAs that will form complementary base pairs with the endogenous Claudin-23 gene transcripts and thereby prevent translation of the Claudin-23 mRNA. For example, a vector can be introduced in vivo such that it is taken up by a cell and directs the transcription of an antisense RNA. Such a vector can remain episomal or become chromosomally integrated, so long as it can be transcribed to produce the desired antisense RNA. Such vectors can be constructed by recombinant DNA technology methods standard in the art. Vectors can be plasmid, viral, or others known in the art used for replication and expression in mammalian cells.

Ribozyme molecules designed to catalytically cleave Claudin-23 mRNA transcripts can also be used to prevent translation of Claudin-23 mRNA thereby inhibiting expression of Claudin polypeptides of the invention (see, e.g., PCT International Publication WO90/11364, published Oct. 4, 1990; U.S. Pat. No. 5,824,519). The ribozymes that can be used in the invention include hammerhead ribozymes (Haseloff and Gerlach, 1988, Nature, 334:585–591), RNA endoribonucleases (hereinafter "Cech-type ribozymes") such as the one which occurs naturally in *Tetrahymena Thermophila* (known as the IVS, or L-19 IVS RNA) and which has been extensively described by Thomas Cech and collaborators (International Patent Application No. WO 88/04300; Been and Cech, 1986, Cell, 47:207–216). As in the antisense approach, the ribozymes can be composed of modified oligonucleotides (e.g. for improved stability, targeting, and the like) and should be delivered to cells which express the human Claudin-23 polypeptide in vivo. A typical method of delivery involves using a DNA construct coding for the ribozyme under the control of a strong constitutive pol II or pol III promoter, so that transfected cells will produce sufficient quantities of the ribozyme to destroy endogenous Claudin-23 messages and inhibit translation. Because ribozymes, unlike antisense molecules, are catalytic, a lower intracellular concentration is required for efficiency.

Alternatively, endogenous Claudin-23 gene expression can be reduced by targeting deoxyribonucleotide sequences complementary to the regulatory region of the target gene (e.g., the target gene's promoter and/or enhancers) to form triple helical structures that prevent transcription of a Claudin-23 gene (see generally, Helene, 1991, Anticancer Drug Des., 6(6):569–584; Helene, et al., 1992, Ann. N.Y. Acad. Sci., 660, 27–36; and Maher, 1992, Bioassays 14(12):807–815).

Antisense nucleic acids, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as, for example, solid phase phosphoramidite chemical synthesis. Oligonucleotides can be synthesized by standard methods known in the art, e.g. by use of an automated DNA synthesizer (such as are commercially available from Biosearch, Applied Biosystems, and the like). As examples, phosphorothioate oligonucleotides may be synthesized by the method of Stein et al., 1988, Nucl. Acids Res. 16:3209. Methylphosphonate oligonucleotides can be prepared by use of controlled pore glass polymer supports (Sarin et al., 1988, Proc. Natl. Acad. Sci. U.S.A. 85:7448–7451). Alternatively, RNA molecules may be generated by in vitro and in vivo transcription of DNA sequences encoding the antisense RNA molecule. Such DNA sequences may be incorporated into a wide variety of vectors that incorporate suitable RNA polymerase-promoters such as the T7 or SP6 polymerase promoters. Alternatively, antisense cDNA constructs that synthesize antisense RNA constitutively or inducibly, depending on the promoter used, can be introduced stably into cell lines.

Endogenous target gene expression can also be reduced by inactivating or "knocking out" the target gene or its promoter using targeted homologous recombination (e.g., see Smithies, et al., 1985, Nature 317:230–234; Thomas and Capecchi, 1987, Cell 51:503–512; Thompson, et al., 1989, Cell 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (see, e.g., Thomas and Capecchi, 1987 and Thompson, 1989, supra), or in model organisms such as *Caenorhabditis elegans* where the "RNA interference" ("RNAi") technique (Grishok A, Tabara H, and Mello C C, 2000, Genetic requirements for inheritance of RNAi in *C. elegans,* Science 287 (5462): 2494–2497), or the introduction of transgenes (Dernburg A F, Zalevsky J, Colaiacovo M P, and Villeneuve A M, 2000, Transgene-mediated cosuppression in the C. elegans germ line, Genes Dev. 14 (13): 1578–1583) are used to inhibit the expression of specific target genes. However this approach can be adapted for use in humans provided the recombinant DNA constructs are directly administered or targeted to the required site in vivo using appropriate viral vectors.

Organisms that have enhanced, reduced, or modified expression of the gene(s) corresponding to the polynucleotide sequences disclosed herein are provided. The desired change in gene expression can be achieved through the use of antisense nucleic acids or ribozymes that bind and/or cleave the mRNA transcribed from the gene (Albert and Morris, 1994, Trends Pharmacol. Sci. 15(7):250–254; Lavarosky et al., 1997, Biochem. Mol. Med. 62(1): 11–22; and Hampel, 1998, Prog. Nucleic Acid Res. Mol. Biol. 58:1–39; all of which are incorporated by reference herein). Transgenic animals that have multiple copies of the gene(s) corresponding to the polynucleotide sequences disclosed herein, produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see, e.g., European Patent No. 0 649 464 B1, incorporated by reference herein). In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, followed by imprecise excision, of transposable elements (Plasterk, 1992, Bioessays 14(9):629–633; Zwaal et al., 1993, Proc. Natl. Acad. Sci. USA 90(16):7431–7435; Clark et al., 1994, Proc. Natl. Acad. Sci. USA 91(2): 719–722; all of which are incorporated by reference herein), or through homologous recombination which can be detected by positive/negative genetic selection strategies (Mansour et al., 1988, Nature 336:348–352; U.S. Pat. Nos. 5,464,764; 5,487,992; 5,627,059; 5,631,153; 5,614,396; 5,616,491; and 5,679,523; all of which are incorporated by reference herein). These organisms with altered gene expression are eukaryotes and typically are mammals. Such organisms are useful for the development of non-human models for the study of disorders involving the corresponding gene(s), and for the development of assay systems for the identification of molecules that interact with the polypeptide product(s) of the corresponding gene(s).

The Claudin polypeptides of the invention themselves can also be employed in inhibiting a biological activity of Claudin-23 in in vitro or in vivo procedures. Encompassed within the invention are extracellular loop domains of Claudin polypeptides of the invention that act as "dominant negative" inhibitors of native Claudin-23 polypeptide function when expressed as fragments or as components of fusion polypeptides. For example, a purified polypeptide domain of the invention can be used to inhibit binding of Claudin polypeptides of the invention to endogenous binding-partners. Such use would effectively block Claudin-23 polypeptide interactions and inhibit Claudin-23 polypeptide activities. In still another aspect of the invention, a soluble form of a Claudin-23 binding partner, which is expressed on epithelial and/or endothelial cells, is used to bind to and competitively inhibit activation of an endogenous Claudin-23 polypeptide. Furthermore, antibodies which bind to Claudin polypeptides of the invention can inhibit Claudin-23 activity and act as antagonists, or as agonists. For example, antibodies that specifically recognize one or more epitopes of Claudin polypeptides of the invention, or epitopes of conserved variants of Claudin polypeptides of the invention, or peptide fragments of a Claudin-23 polypeptide can be used in the invention to inhibit Claudin-23 activity (antagonistic antibodies). Agonistic antibodies bind to Claudin polypeptides of the invention or binding partners and increase Claudin-23 polypeptide activity by causing constitutive intracellular signaling (or "ligand mimicking"), or by preventing the binding of a native inhibitor of Claudin-23 polypeptide activity. Antibodies which bind to Claudin-23 polypeptides include, but are not limited to, polyclonal antibodies, monoclonal antibodies (mAbs), human (also called "fully human") antibodies, humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Alternatively, purified and modified Claudin polypeptides of the invention can be administered to modulate interactions between Claudin polypeptides of the invention and Claudin-23 binding partners that are not membrane-bound. Such an approach will allow an alternative method for the modification of human Claudin-23-influenced bioactivity.

Polypeptides of the invention may be used to identify antagonists and agonists from cells, cell-free preparations, chemical libraries, and natural product mixtures. The antagonists and agonists may be natural or modified substrates, ligands, enzymes, receptors, etc. of the polypeptides of the instant invention, or may be structural or functional mimetics of the polypeptides. Potential antagonists of the instant invention may include small molecules, peptides and antibodies that bind to and occupy a binding site of the inventive polypeptides or a binding partner thereof, causing them to be unavailable to bind to their natural binding partners and therefore preventing normal biological activity. Potential agonists include small molecules, peptides and antibodies which bind to the instant polypeptides or binding partners thereof, and elicit the same or enhanced biologic effects as those caused by the binding of the polypeptides of the instant invention. Peptide agonists and antagonists of the polypeptides of the invention can be identified and utilized according to known methods (see, for example, WO 00/24782 and WO 01/83525, which are incorporated by reference herein).

An approach to development of therapeutic agents is peptide library screening. The interaction of a protein ligand with its receptor often takes place at a relatively large interface. However, as demonstrated for human growth hormone and its receptor, only a few key residues at the interface contribute to most of the binding energy (Clackson et al., 1995. *Science* 267: 383–386). The bulk of the protein ligand merely displays the binding epitopes in the right topology or serves functions unrelated to binding. Thus, molecules of only "peptide" length (2 to 90 amino acids) can bind to the receptor protein or binding partner of even a large protein ligand such as a polypeptide of the invention. Such peptides may mimic the bioactivity of the large protein ligand ("peptide agonists") or, through competitive binding, inhibit the bioactivity of the large protein ligand ("peptide antagonists"). Exemplary peptide agonists and antagonists of polypeptides of the invention may comprise a domain of a naturally occurring molecule or may comprise randomized sequences. The term "randomized" as used to refer to peptide sequences refers to fully random sequences (e.g., selected by phage display methods or RNA-peptide screening) and sequences in which one or more residues of a naturally occurring molecule is replaced by an amino acid residue not appearing in that position in the naturally occurring molecule. Phage display peptide libraries have emerged as a powerful method in identifying such peptide agonists and antagonists. See, for example, Scott et al., 1990, *Science* 249: 386; Devlin et al., 1990, *Science* 249: 404; U.S. Pat. Nos. 5,223,409; 5,733,731; 5,498,530; 5,432,018; 5,338,665; 5,922,545; WO 96/40987; and WO 98/15833 (each of which is incorporated by reference in its entirety). In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides. The peptide sequences may also suggest which residues may be safely replaced by alanine scanning or by mutagenesis at the DNA level. Mutagenesis libraries may be created and screened to further optimize the sequence of the best binders (Lowman, 1997, *Ann. Rev. Biophys. Biomol. Struct.* 26: 401–424). Another biological approach to screening soluble peptide mixtures uses yeast for expression and secretion (Smith et al., 1993, *Mol. Pharmacol.* 43: 741–748) to search for peptides with favorable therapeutic properties. Hereinafter, this and related methods are referred to as "yeast-based screening." A peptide library can also be fused to the carboxyl terminus of the lac repressor and expressed in *E. coli*. Another *E. coli*-based method allows display on the cell's outer membrane by fusion with a peptidoglycan-associated lipoprotein (PAL). Hereinafter, these and related methods are collectively referred to as "*E. coli* display." In another method, translation of random RNA is halted prior to ribosome release, resulting in a library of polypeptides with their associated RNA still attached. Hereinafter, this and related methods are collectively referred to as "ribosome display." Other methods employ peptides linked to RNA; for example, PROfusion technology, Phylos, Inc. (see, for example, Roberts and Szostak, 1997. *Proc. Natl. Acad. Sci. USA* 94: 12297–12303). Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells and Lowman, 1992, *Curr. Opin. Biotechnol.* 3: 355–362.

In the case of known bioactive peptides, rational design of peptide ligands with favorable therapeutic properties can be completed. In such an approach, one makes stepwise changes to a peptide sequence and determines the effect of the substitution upon bioactivity or a predictive biophysical property of the peptide (e.g., solution structure). Hereinafter, these techniques are collectively referred to as "rational design." In one such technique, one makes a series of peptides in which one replaces a single residue at a time with alanine. This technique is commonly referred to as an "alanine walk" or an "alanine scan." When two residues (contiguous or spaced apart) are replaced, it is referred to as a "double alanine walk." The resultant amino acid substitutions can be used alone or in combination to result in a new peptide entity with favorable therapeutic properties. Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed (see, e.g., Takasaki et al., 1997, *Nature Biotech.* 15: 1266–1270). Hereinafter, these and related methods are referred to as "protein structural analysis." These analytical methods may also be used to investigate the interaction between a receptor protein and peptides selected by phage display, which may suggest further modification of the peptides to increase binding affinity.

Peptide agonists and antagonists of polypeptides of the invention may be covalently linked to a vehicle molecule. The term "vehicle" refers to a molecule that prevents degradation and/or increases half-life, reduces toxicity, reduces immunogenicity, or increases biological activity of a therapeutic protein. Exemplary vehicles include an Fc domain or a linear polymer (e.g., polyethylene glycol (PEG), polylysine, dextran, etc.); a branched-chain polymer (see, for example, U.S. Pat. Nos. 4,289,872; 5,229,490; WO 93/21259); a lipid; a cholesterol group (such as a steroid); a carbohydrate or oligosaccharide (e.g., dextran); or any natural or synthetic protein, polypeptide or peptide that binds to a salvage receptor.

Antibodies to Claudin Polypeptides

Antibodies that are immunoreactive with the polypeptides of the invention are provided herein. Such antibodies specifically bind to the polypeptides via the antigen-binding sites of the antibody (as opposed to non-specific binding). In the invention, specifically binding antibodies are those that will specifically recognize and bind with Claudin polypeptides of the invention, homologues, and variants, but not with other molecules. In one embodiment, the antibodies are specific for the polypeptides of the invention and do not cross-react with other polypeptides. In this manner, the Claudin polypeptides of the invention, fragments, variants, fusion polypeptides, and the like, as set forth above, can be employed as "immunogens" in producing antibodies immunoreactive therewith.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding (C. A. Janeway, Jr. and P. Travers, *Immuno Biology* 3:9 (Garland Publishing Inc., 2nd ed. 1996)). Because folded polypeptides have complex surfaces, the number of epitopes available is quite numerous; however, due to the conformation of the polypeptide and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes can be identified by any of the methods known in the art. Thus, one aspect of the invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies can be prepared by conventional techniques. See, for example, *Monoclonal Antibodies, Hybridomas: A New Dimension in Biological Analyses,* Kennet et al. (eds.), Plenum Press, New York (1980); and *Antibodies: A laboratory Manual,* Harlow and Land (eds.), Cold Spring Harbor Laboratory Press, Cold Spring Harbor, N.Y., (1988); Kohler and Milstein, (U.S. Pat. No. 4,376,110); the human B-cell hybridoma technique (Kosbor et al., 1983, Immunology Today 4:72; Cole et al., 1983, Proc. Natl. Acad. Sci. USA 80:2026–2030); and the EBV-hybridoma technique (Cole et al., 1985, Monoclonal Antibodies And Cancer Therapy, Alan R. Liss, Inc., pp. 77–96). Hybridoma cell lines that produce monoclonal antibodies specific for the polypeptides of the invention are also contemplated herein. Such hybridomas can be produced and identified by conventional techniques. The hybridoma producing the mAb of this invention may be cultivated in vitro or in vivo. Production of high titers of mAbs in vivo makes this the most common method of production. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. For the production of antibodies, various host animals may be immunized by injection with one or more of the following: a Claudin-23 polypeptide, a fragment of a Claudin-23 polypeptide, a functional equivalent of a Claudin-23 polypeptide, or a mutant form of a Claudin-23 polypeptide. Such host animals may include, but are not limited to rabbits, mice and rats. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum. The monoclonal antibodies can be recovered by conventional techniques. Such monoclonal antibodies may be of any immunoglobulin class including IgG, IgM, IgE, IgA, IgD, and any subclass thereof.

In addition, techniques developed for the production of "chimeric antibodies" (Takeda et al., 1985, Nature, 314: 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region. The monoclonal antibodies of the invention also include humanized versions of murine monoclonal antibodies. Such humanized antibodies can be prepared by known techniques and offer the advantage of reduced immunogenicity when the antibodies are administered to humans. In one embodiment, a humanized monoclonal antibody comprises the variable region of a murine antibody (or just the antigen-binding site thereof) and a constant region derived from a human antibody. Alternatively, a humanized antibody fragment can comprise the antigen-binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989). and Winter and Harris (*TIPS* 14:139, Can, 1993). Procedures to generate antibodies transgenically can be found in GB 2,272,440U.S. Pat. No. 5,569,825 and 5,545,806 and related patents claiming priority therefrom, all of which are incorporated by reference herein. Preferably, for use in humans, the antibodies are human or humanized; techniques for creating such human or humanized antibodies are also well known and are commercially available from, for example, Medarex Inc. (Princeton, N.J.) and Abgenix Inc. (Fremont, Calif.).

Antigen-binding antibody fragments that recognize specific epitopes may be generated by known techniques. For example, such fragments include, but are not limited to: the F(ab')2 fragments which can be produced by pepsin digestion of the antibody molecule and the Fab fragments which can be generated by reducing the disulfide bridges of the (ab')2 fragments. Alternatively, Fab expression libraries may be constructed (Huse et al., 1989, Science, 246:1275-1281) to allow rapid and easy identification of monoclonal Fab fragments with the desired specificity. Techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can also be adapted to produce single chain antibodies against Claudin-23 gene products. Single chain antibodies are formed by linking the heavy and light chain fragments of the Fv region via an amino acid bridge, resulting in a single chain polypeptide. In addition, antibodies to a Claudin-23 polypeptide can, in turn, be utilized to generate anti-idiotype antibodies that "mimic" a Claudin-23 polypeptide and that may bind to a Claudin-23 polypeptide using techniques well known to those skilled in the art (see, e.g., Greenspan & Bona, 1993, FASEB J 7(5):437–444; and Nissinoff, 1991, J. Immunol. 147(8): 2429–2438).

Screening procedures by which such antibodies can be identified are well known, and can involve immunoaffinity chromatography, for example. Antibodies can be screened for agonistic (i.e., ligand-mimicking) properties. Such antibodies, upon binding to cell surface Claudin-23, induce biological effects (e.g., transduction of biological signals) similar to the biological effects induced when a Claudin-23 binding partner binds to a cell surface Claudin-23. Agonistic antibodies can be used to induce Claudin-23-mediated activities, such as epithelial barrier formation, stimulatory pathways, or intercellular communication. Those antibodies that can block binding of the Claudin polypeptides of the invention to binding partners for Claudin-23 can be used to inhibit Claudin-23-mediated epithelial barrier formation, intercellular communication, or co-stimulation that results from such binding. Such blocking antibodies can be identified using any suitable assay procedure, such as by testing antibodies for the ability to inhibit binding of Claudin-23 to certain cells expressing a Claudin-23 binding partner. Alternatively, blocking antibodies can be identified in assays for the ability to inhibit a biological effect that results from binding of a Claudin-23 to target cells, such as epithelial barrier formation, using assays described herein. Such an antibody can be employed in an in vitro procedure, or administered in vivo to inhibit a biological activity mediated by the entity that generated the antibody. Disorders caused or exacerbated (directly or indirectly) by the interaction of Claudin-23 with cell surface binding partner receptor thus can be treated. A therapeutic method involves in vivo administration of a blocking antibody to a mammal in an amount effective in inhibiting Claudin-23 binding partner-mediated biological activity. Human or humanized antibodies can be used in such therapeutic methods. In one embodiment, an antigen-binding antibody fragment is employed. Compositions comprising an antibody that is directed against Claudin-23, and a physiologically acceptable diluent, excipient, or carrier, are provided herein. Suitable components of such compositions are as described below for compositions containing Claudin polypeptides of the invention.

Also provided herein are conjugates comprising a detectable (e.g., diagnostic) or a therapeutic agent, attached to the antibody. Examples of such agents are presented above. The conjugates find use in in vitro or in vivo procedures. The antibodies of the invention can also be used in assays to detect the presence of the polypeptides or fragments of the invention, either in vitro or in vivo. The antibodies also can be employed in purifying polypeptides or fragments of the invention by immunoaffinity chromatography.

Rational Design of Compounds that Interact with Claudin Polypeptides

The goal of rational drug design is to produce structural analogs of biologically active polypeptides of interest or of small molecules with which they interact, e.g., inhibitors, agonists, antagonists, and the like. Any of these examples can be used to fashion drugs which are more active or stable forms of a polypeptide or which enhance or interfere with the function of a polypeptide in vivo (Hodgson J., 1991, Biotechnology 9:19–21, incorporated herein by reference). In one approach, the three-dimensional structure of a polypeptide of interest, or of a polypeptide-inhibitor complex, is determined by x-ray crystallography, by nuclear magnetic resonance, or by computer homology modeling or, most typically, by a combination of these approaches. Both the shape and charges of the polypeptide must be ascertained to elucidate the structure and to determine active site(s) of the polypeptide. Less often, useful information regarding the structure of a polypeptide may be gained by modeling based on the structure of homologous polypeptides. In both cases, relevant structural information is used to design analogous Claudin-like molecules, to identify efficient inhibitors, or to identify small molecules that may bind a Claudin of the invention. Useful examples of rational drug design may include molecules which have improved activity or stability as shown by Braxton S and Wells J A (1992, Biochemistry 31:7796–7801) or which act as inhibitors, agonists, or antagonists of native peptides as shown by Athauda S B et al. (1993, J Biochem 113:742–746), incorporated herein by reference. The use of Claudin-23 polypeptide structural information in molecular modeling software systems to assist in inhibitor design and inhibitor-Claudin-23 polypeptide interaction is also encompassed by the invention. A particular method of the invention comprises analyzing the three-dimensional structure of Claudin polypeptides of the invention for likely binding sites of substrates, synthesizing a new molecule that incorporates a predictive reactive site, and assaying the new molecule as described further herein.

It is also possible to isolate a target-specific antibody, selected by functional assay, as described further herein, and then to solve its crystal structure. This approach, in principle, yields a pharmacore upon which subsequent drug design can be based. It is possible to bypass polypeptide crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

Assays of Activities of Claudin Polypeptides of the Invention

The purified Claudin-23 polypeptides of the invention (including polypeptides, fragments, variants, oligomers, and other forms) are useful in a variety of assays. For example, a Claudin-23 molecule of the invention can be used to identify agonists and/or antagonists of Claudin-23 polypeptides of the invention, which can be used to modulate Claudin biological activities such as tight junction formation or endothelial or epithelial barrier formation. In one embodiment, the Claudin-23 polypeptides of the invention are used in binding assays to identify molecules (binding partners) that bind to Claudin-23, and then these molecules are tested in additional assays for modulation of Claudin-23 polypeptide activity as described herein. In one embodiment of these methods of the invention, the determination of Claudin-23 polypeptide activity comprises an assessment of transcription and/or translation of skin differentiation markers such as, but not limited to, filaggrin, profilaggrin, involucrin, and keratin markers (such as K1, K2, K2e, K2p, K4, K5, K6, K8, K9, K10, K13, K14, K16, K17, K18, K19, and the like) by conventional techniques, for example the use of differentiation marker-specific probes.

Assays to Identify Binding Partners. Claudin-23 polypeptides and fragments thereof can be used to identify binding partners. For example, they can be tested for the ability to bind a candidate binding partner in any suitable assay, such as a conventional binding assay. To illustrate, a Claudin-23 polypeptide can be labeled with a detectable reagent (e.g., a radionuclide, chromophore, enzyme that catalyzes a colorimetric or fluorometric reaction, and the like). The labeled polypeptide is contacted with cells expressing the candidate binding partner. The cells then are washed to remove unbound labeled polypeptide, and the presence of cell-bound label is determined by a suitable technique, chosen according to the nature of the label.

One example of a binding assay procedure is as follows. A recombinant expression vector containing the candidate binding partner cDNA is constructed. CV1-EBNA-1 cells in 10 cm$^2$ dishes are transfected with this recombinant expression vector. CV-1/EBNA-1 cells (ATCC CRL 10478) constitutively express EBV nuclear antigen-1 driven from the CMV Immediate-early enhancer/promoter. CV1-EBNA-1 was derived from the African Green Monkey kidney cell line CV-1 (ATCC CCL 70), as described by McMahan et al., (*EMBO J*. 10:2821, 1991). The transfected cells are cultured for 24 hours, and the cells in each dish then are split into a 24-well plate. After culturing an additional 48 hours, the transfected cells (about 4×10$^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion polypeptide made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization. The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc polypeptide that has bound to the cells. In all assays, non-specific binding of $^{125}$I-antibody is assayed in the absence of the Fc fusion polypeptide/Fc, as well as in the presence of the Fc fusion polypeptide and a 200-fold molar excess of unlabeled mouse anti-human IgG antibody. Cell-bound $^{125}$I-antibody is quantified on a Packard Autogamma counter. Affinity calculations (Scatchard, *Ann. N. Y. Acad. Sci.* 51:660, 1949) are generated on RS/1 (BBN Software, Boston, Mass.) run on a Microvax computer. Binding can also be detected using methods that are well suited for high-throughput screening procedures such as scintillation proximity assays (Udenfriend et al., 1985, Proc Natl Acad Sci USA 82: 8672–8676), homogeneous time-resolved fluorescence methods (Park et al., 1999, Anal Biochem 269: 94–104), fluorescence resonance energy transfer (FRET) methods (Clegg R M, 1995, Curr Opin Biotechnol 6: 103–110), or methods that measure any changes in surface plasmon resonance when a bound polypeptide is exposed to a potential binding partner, such methods using, for example, a biosensor such as that supplied by Biacore AB (Uppsala, Sweden).

Compounds that can be assayed for binding to Claudin polypeptides of the invention include but are not limited to small organic molecules, such as those that are commercially available—often as part of large combinatorial chemistry compound 'libraries'—from companies such as Sigma-Aldrich (St. Louis, Mass.), Arqule (Woburn, Ma.), Enzymed (Iowa City, Iowa), Maybridge Chemical Co.(Trevillett, Cornwall, UK), MDS Panlabs (Bothell, Wash.), Pharmacopeia (Princeton, N.J.), and Trega (San Diego, Calif.). Small organic molecules for screening using these assays are usually less than 10K molecular weight and can possess a number of physicochemical and pharmacological properties which enhance cell penetration, resist degradation, and/or prolong their physiological half-lives (Gibbs, J., 1994, Pharmaceutical Research in Molecular Oncology, *Cell* 79(2): 193–198). Compounds including natural products, inorganic chemicals, and biologically active materials such as proteins and toxins can also be assayed using these methods for the ability to bind to Claudin-23 polypeptides of the invention.

Specific screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, as well as more traditional heterogeneous assay formats such as enzyme-linked immunosorbant assays (ELISA) or radioimmunoassays. Homogeneous assays are "mix and read" assays that are very amenable to robotic application, whereas heterogeneous assays require separation of bound analyte from free by more complex unit operations such as filtration, centrifugation or washing. These assays are utilized to detect a wide variety of specific biomolecular interactions and the inhibition thereof by small organic molecules, including protein-protein, receptor-ligand, enzyme-substrate, etc. These assay methods and techniques are well known in the art and are described more fully in the following: High Throughput Screening: The Discovery of Bioactive Substances, John P. Devlin (ed.), Marcel Dekker, New York, 1997, ISBN: 0-8247-0067-8; and the internet sites of lab-robotics.org and sbsonline.org. The screening assays of the present invention are amenable to high throughput screening of chemical libraries and are suitable for the identification of small molecule drug candidates, antibodies, peptides, and other antagonists and/or agonists.

Yeast Two-Hybrid or "Interaction Trap" Assays. Where a Claudin-23 polypeptide binds or potentially binds to another polypeptide (such as, for example, in a receptor-ligand interaction), the polynucleotide encoding a Claudin-23 polypeptide can also be used in interaction trap assays (such as, for example, described in Gyuris et al., 1993, Cell 75:791–803) to identify polynucleotides encoding the other polypeptide with which binding occurs or to identify inhibitors of the binding interaction. Polypeptides involved in these binding interactions can also be used to screen for peptide or small molecule inhibitors or agonists of the binding interaction.

Competitive Binding Assays. Another type of suitable binding assay is a competitive binding assay. To illustrate, biological activity of a variant can be determined by assaying for the variant's ability to compete with the native polypeptide for binding to the candidate binding partner. Competitive binding assays can be performed by conventional methodology. Reagents that can be employed in competitive binding assays include radiolabeled Claudin-23 and intact cells expressing Claudin-23 (endogenous or recombinant) on the cell surface. For example, a radiolabeled soluble Claudin-23 fragment can be used to compete with a soluble Claudin-23 variant for binding to cell surface receptors. Instead of intact cells, one could substitute a soluble binding partner/Fc fusion polypeptide bound to a solid phase through the interaction of Polypeptide A or Polypeptide G (on the solid phase) with the Fc moiety. Chromatography columns that contain Polypeptide A and Polypeptide G include those available from Pharmacia Biotech, Inc., Piscataway, N.J.

Assays to Identify Modulators of Intercellular Communication or Cell Activity. The influence of Claudin polypeptides of the invention on intercellular communication or cell activity can be manipulated to control these activities in target cells. For example, the disclosed Claudin polypeptides of the invention, polynucleotides encoding the disclosed Claudin polypeptides of the invention, or agonists or antagonists of such polypeptides can be administered to a cell or group of cells to induce, enhance, suppress, or arrest cellular communication or activity in the target cells. Identification of Claudin polypeptides of the invention, agonists or antagonists that can be used in this manner can be carried out via a variety of assays known to those skilled in the art. Included in such assays are those that evaluate the ability of a Claudin-23 polypeptide to influence intercellular communication or cell activity. Such an assay would involve, for example, the analysis of cell interaction in the presence of a Claudin-23 polypeptide. In such an assay, one would determine a rate of communication or cell stimulation in the presence of a Claudin-23 polypeptide and then determine if such communication or cell stimulation is altered in the presence of a candidate agonist or antagonist or another Claudin-23 polypeptide. Exemplary assays for this aspect of the invention include cytokine secretion assays, T-cell co-stimulation assays, and mixed lymphocyte reactions involving antigen presenting cells and T cells. These assays are well known to those skilled in the art.

In another aspect, the invention provides a method of detecting the ability of a test compound to affect the intercellular communication or co-stimulatory activity of a cell. In this aspect, the method comprises: (1) contacting a first group of target cells with a test compound including a Claudin-23 binding partner polypeptide or fragment thereof under conditions appropriate to the particular assay being used; (2) measuring the net rate of intercellular communication or co-stimulation among the target cells; and (3) observing the net rate of intercellular communication or co-stimulation among control cells containing a Claudin-23 binding partner polypeptide or fragment thereof, in the absence of a test compound, under otherwise identical conditions as the first group of cells. In this embodiment, the net rate of intercellular communication or co-stimulation in the control cells is compared to that of the cells treated with both a Claudin-23 molecule as well as a test compound. The comparison will provide a difference in the net rate of intercellular communication or co-stimulation such that an effector of intercellular communication or co-stimulation can be identified. The test compound can function as an effector by either activating or up-regulating, or by inhibiting or down-regulating intercellular communication or co-stimulation, and can be detected through this method.

Cell Proliferation, Cell Death, Cell Differentiation, and Cell Adhesion Assays. A polypeptide of the invention may exhibit cytokine, cell proliferation (either inducing or inhibiting) or cell differentiation (either inducing or inhibiting) activity or may induce production of other cytokines in certain cell populations. Many polypeptide factors discovered to date, including all known cytokines, have exhibited activity in one or more factor dependent cell proliferation assays, and hence the assays serve as a convenient confirmation of cytokine activity. The activity of a polypeptide of the invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK. The activity of a Claudin-23 polypeptide of the invention may, among other means, be measured by the following methods:

Assays for cell movement and adhesion include, without limitation, those described in: Current Protocols in Immunology, Ed by Coligan et al., Pub. Greene Publishing Associates and Wiley-Interscience (Chapter 6.12, Measurement of alpha and beta Chemokines 6.12.1–6.12.28; Taub et al., J. Clin. Invest. 95:1370–1376, 1995; Lind et al., APMIS 103: 140–146, 1995; Muller et al., Eur. J. Immunol. 25:1744–1748; Gruber et al. J. Immunol. 152:5860–5867, 1994; Johnston et al., J. Immunol. 153:1762–1768, 1994.

Assays for cadherin adhesive and invasive suppressor activity include, without limitation, those described in: Hortsch et al. J Biol Chem 270 (32): 18809–18817, 1995; Miyaki et al. Oncogene 11: 2547–2552, 1995; Ozawa et al. Cell 63:1033–1038, 1990.

Diagnostic and Other Uses of Claudin Polypeptides of the Invention and Polynucleotides The polynucleotides encoding the Claudin polypeptides of the invention can be used for numerous diagnostic or other useful purposes. The polynucleotides of the invention can be used to express recombinant polypeptide for analysis, characterization or therapeutic use; as markers for tissues in which the corresponding polypeptide is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in subjects to identify potential genetic disorders; as probes to hybridize and thus discover novel, related DNA sequences; as a source of information to derive PCR primers for genetic fingerprinting; as a probe to "subtract-out" known sequences in the process of discovering other novel nucleic acid molecules; for selecting and making oligomers for attachment to a "gene chip" or other support, including for examination of expression patterns; to raise anti-polypeptide antibodies using DNA immunization techniques; as an antigen to raise anti-DNA antibodies or elicit another immune response, and for gene therapy. Uses of Claudin polypeptides of the invention and fragmented polypeptides include, but are not limited to, the following: purifying polypeptides and measuring the activity thereof; delivery agents; therapeutic and research reagents; molecular weight and isoelectric focusing markers; controls for peptide fragmentation; identification of unknown polypeptides; and preparation of antibodies. Any or all polynucleotides suitable for these uses are capable of being developed into reagent grade or kit format for commercialization as products. Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Probes and Primers. Among the uses of a disclosed Claudin-23 polynucleotide, and combinations of fragments thereof, is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence. The basic parameters affecting the choice of hybridization conditions and guidance for devising suitable conditions are set forth by Sambrook et al., 1989 and are described in detail above. Using knowledge of the genetic code in combination with the amino acid sequences set forth above, sets of degenerate oligonucleolides can be prepared. Such oligonucleotides are useful as primers, e.g., in polymerase chain reactions (PCR), whereby DNA fragments are isolated and amplified. In certain embodiments, degenerate primers can be used as probes for non-human genetic libraries. Such libraries include, but are not limited to, cDNA libraries, genomic libraries, and electronic EST (express sequence tag) or DNA libraries. Homologous sequences identified by this method can then be used as probes to identify Claudin-23 molecules from other species.

Diagnostics and Gene Therapy. The polynucleotides encoding Claudin polypeptides of the invention, and the disclosed fragments and combinations of these polynucleotides can be used by one skilled in the art using well-known techniques to analyze abnormalities associated with the genes corresponding to these polypeptides. This enables one to distinguish conditions in which this marker is rearranged or deleted. In addition, polynucleotides of the invention or a fragment thereof can be used as a positional marker to map other genes of unknown location. The DNA can be used in developing treatments for any disorder mediated (directly or indirectly) by defective, or insufficient amounts of, the genes corresponding to the polynucleotides of the invention. Disclosure herein of native nucleotide sequences permits the detection of defective genes, and the replacement thereof with normal genes. Defective genes can be detected in in vitro diagnostic assays, and by comparison of a native nucleotide sequence disclosed herein with that of a gene derived from a person suspected of harboring a defect in this gene.

Methods of Screening for Binding Partners. The Claudin polypeptides of the invention each can be used as reagents in methods to screen for or identify binding partners. For example, the Claudin polypeptides of the invention can be attached to a solid support material and may bind to their binding partners in a manner similar to affinity chromatography. In particular embodiments, a polypeptide is attached to a solid support by conventional procedures. As one example, chromatography columns containing functional groups that will react with functional groups on amino acid side chains of polypeptides are available (Pharmacia Biotech, Inc., Piscataway, N.J.). In an alternative, a polypeptide/Fc polypeptide (as discussed above) is attached to Polypeptide A- or Polypeptide G-containing chromatography columns through interaction with the Fc moiety. The Claudin polypeptides of the invention also find use in identifying cells that express a binding partner on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing potential binding-partner-expressing cells are contacted with the solid phase having the polypeptides thereon. Cells expressing the binding partner on the cell surface bind to the fixed polypeptides, and unbound cells are washed away. Alternatively, Claudin polypeptides of the invention can be conjugated to a detectable moiety, then incubated with cells to be tested for binding partner expression. After incubation, unbound-labeled matter is removed and the presence or absence of the detectable moiety on the cells is determined. In a further alternative, mixtures of cells suspected of expressing the binding partner are incubated with biotinylated polypeptides. Incubation periods are typically at least one hour in duration to ensure sufficient binding. The resulting mixture is then passed through a column packed with avidin-coated beads, whereby the high affinity of biotin for avidin provides binding of the desired cells to the beads. Procedures for using avidin-coated beads are known (see Berenson, et al., *J. Cell. Biochem.*, 10D:239, 1986). Washing to remove unbound material, and the release of the bound cells, are performed using conventional methods. In some instances, the above methods for screening for or identifying binding partners may also be used or modified to isolate or purify such binding partner molecules or cells expressing them.

Measuring Biological Activity. Polypeptides also find use in measuring the biological activity of Claudin-23-binding polypeptides in terms of their binding affinity. The polypeptides thus can be employed by those conducting "quality assurance" studies, e.g., to monitor shelf life and stability of polypeptide under different conditions. For example, the polypeptides can be employed in a binding affinity study to measure the biological activity of a binding partner polypeptide that has been stored at different temperatures, or produced in different cell types. The polypeptides also can be used to determine whether biological activity is retained after modification of a binding partner polypeptide (e.g., chemical modification, truncation, mutation, etc.). The binding affinity of the modified polypeptide is compared to that of an unmodified binding polypeptide to detect any adverse impact of the modifications on biological activity of the binding polypeptide. The biological activity of a binding polypeptide thus can be ascertained before it is used in a research study, for example.

Carriers and Delivery Agents. The polypeptides also find use as carriers for delivering agents attached thereto to cells bearing identified binding partners. The polypeptides thus can be used to deliver diagnostic or therapeutic agents to such cells (or to other cell types found to express binding partners on the cell surface) in in vitro or in vivo procedures. Detectable (diagnostic) and therapeutic agents that can be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating polypeptides, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu. Such agents can be attached to the polypeptide by any suitable conventional procedure. The polypeptide comprises functional groups on amino acid side chains that can be reacted with functional groups on a desired agent to form covalent bonds, for example. Alternatively, the polypeptide or agent can be derivatized to generate or attach a desired reactive functional group. The derivatization can involve attachment of one of the bifunctional coupling reagents available for attaching various molecules to polypeptides (Pierce Chemical Company, Rockford, Ill.). A number of techniques for radiolabeling polypeptides are known. Radionuclide metals can be attached to polypeptides by using a suitable bifunctional chelating agent, for example. Conjugates comprising polypeptides and a suitable diagnostic or therapeutic agent (preferably covalently linked) are thus prepared. The conjugates are administered or otherwise employed in an amount appropriate for the particular application.

Cancer Diagnostics. Where Claudin-23 is down-regulated in cancer conditions detecting the presence of Claudin-23 polypeptide or polynucleotides can be used in cancer prognosis and diagnosis. The invention provides a method of diagnosing a cell proliferative disorder (e.g., a tumor) in a subject, comprising obtaining a fluid sample (e.g., blood, serum, urine, saliva, bile, lymph fluid, or spinal fluid) or a tissue biopsy (e.g., lymph, hepatic, or spleen tissue) or both fluid and biopsy samples from a subject and detecting a change in expression of Claudin-23. For example, methods include detecting down-regulation of expression of a Claudin-23 compared to a control sample. The method of detection may be any number of methods known in the art including radioimmunoassays, ELIZAs, Western blots, Northern or Southern Blots, polynucleotide amplification techniques, and the like.

Treating Diseases with Claudin Polypeptides, Agonists, and Antagonists Thereof

It is anticipated that the Claudin-23 polypeptides, fragments, variants, antagonists, agonists, antibodies, and binding partners of the invention will be useful for treating medical conditions and diseases including, but not limited to, conditions involving epithelial or endothelial barrier function or ion transport as described herein. The therapeutic molecule or molecules to be used will depend on the etiology of the condition to be treated and the biological pathways involved, and variants, fragments, and binding partners of Claudin polypeptides of the invention may have effects similar to or different from Claudin polypeptides of the invention. For example, an antagonist of the tight junction formation activity of Claudin polypeptides of the invention may be selected for treatment of conditions involving tight junction formation, but a particular fragment of a given Claudin-23 polypeptide may also act as an effective dominant negative antagonist of that activity. In the following paragraphs "Claudin-23 antagonists" or "antagonists of Claudin-23" refers to fragments of Claudin-23 polypeptides of the invention having a dominant negative effect on Claudin-23 polypeptide activity, polynucleotides such as antisense polynucleotides or silencing RNAs that decrease levels of Claudin-23 polypeptide expression, antagonistic antibodies, binding partners, and other Claudin-23 antagonists of the invention that function as antagonists of Claudin-23 polypeptide activity. In the following paragraphs "Claudin-23 agonists" or "agonists of Claudin-23" refers to Claudin-23 polypeptides of the invention having Claudin-23 polypeptide activity, polynucleotides that increase levels of Claudin-23 polypeptide expression, soluble forms, fragments, variants, antibodies, binding partners, and other Claudin-23 agonists of the invention that function as agonists of Claudin-23 polypeptide activity. It is understood that a specific molecule or molecules can be selected from those provided as embodiments of the invention by individuals of skill in the art, according to the biological and therapeutic considerations described herein. In one aspect, the invention entails administering compositions comprising a Claudin-23 polynucleotide and/or a Claudin-23 polypeptide and/or an agonist thereof to cells in vitro, to cells ex vivo, to cells in vivo, and/or to a multicellular organism. In still another aspect of the invention, the compositions comprise administering a Claudin-23-encoding polynucleotide for expression of a Claudin-23 polypeptide in a host organism for treatment of disease or disorder. Particularly useful in this regard is expression in a human subject for treatment of a dysfunction associated with aberrant (e.g., decreased) endogenous activity of a human Claudin-23 polypeptide. Furthermore, the invention encompasses the administration to cells and/or organisms of compounds found to increase the endogenous activity of Claudin polypeptides of the invention. One example of compounds that increases Claudin-23 polypeptide activity are agonistic antibodies, such as human or humanized antibodies, that bind to Claudin polypeptides of the invention or binding partners and increase Claudin-23 polypeptide activity by causing constitutive intracellular signaling (or "ligand mimicking"), or by preventing the binding of a native inhibitor of Claudin-23 polypeptide activity.

The invention encompasses the use of agonists of Claudin-23 activity to treat or ameliorate the symptoms of a disease for which increased Claudin-23 activity is beneficial. Such diseases include, but are not limited to, skin-related diseases as described in more detail below; inflammatory diseases (such as inflammatory bowel disease, inflammatory eye disease, herpetic stromal keratitis, and inflammatory eye disease associated with smoking and macular degeneration); allergies, including allergic rhinitis, contact dermatitis, atopic dermatitis and asthma; cell proliferative disorders including neoplasms/cancers and metastasis of cancer cells; ion transport disorders such as magnesium transport defects in the kidney; exposure to Clostridium perfringens enterotoxin (CPE); sudden infant death syndrome (SIDS); multiple sclerosis (MS); autoimmune encephalomyelitis; optic neuritis; progressive multifocal leukoencephalopathy (PML); and demyelinating neuropathy.

The disclosed Claudin-23 polypeptides and agonists thereof, including compositions and combination therapies described herein, are useful in medicines and methods of treatment involving disorders of the epithelium, such as disorders of the skin and/or of the mucous membranes. Such disorders include differentiative and proliferative disorders of the epithelium; hyperplastic growth of epithelium; acantholytic diseases, including Darier's disease, keratosis follicularis and pemphigus vulgaris; paraneoplastic pemphigus; aphthous stomatitis; bullous pemphigoid; epidermolysis bullosa, including bullous congenital icthyosiform erythroderma and Dowling-Meara type; pachyonychia congenita; hyperkeratosis, including epidermolytic hyperkeratosis; icthyosis, including icthyosis bullosa of Siemens and icthyosis vulgaris; palmoplantar keratoderma, including epidermolytic and non-epidermolytic palmoplantar keratoderma; pachyonychia congenita, including Jadassohn-Lewandowsky type; white sponge nevus; tricho-dento-osseous syndrome; tooth agenesis; autosomal dominant craniosyntosis, including Boston type; Papillon-Lefevre syndrome; Haim-Munk syndrome; prebubertal periodontis; burns; eczema; erythema, including erythema multiforme and erythema multiforme bullosum (Stevens-Johnson syndrome); inflammatory skin disease, including psoriasis, leukocutoclastic vasculitis, allergic contact dermatitis, pemphigus vulgaris, erythema multifome; lupus erythematosus; lichen planus; linear IgA bullous disease (chronic bullous dermatosis of childhood); loss of skin elasticity; fragility of the epidermis; ulcerations, including chronic ulcerations, diabetes-associated ulcerations, aphthous stomatitis, and mucosal surface ulcers; neutrophilic dermatitis (Sweet's syndrome); pityriasis rubra pilaris; pyoderma gangrenosum; acne; acne rosacea; alopecia areata; and toxic epidermal necrolysis; Kaposi's sarcoma; and erythema nodosum leprosum.

Agonists of Claudin-23 can be used to induce hair growth in patients in need thereof, for example, to treat alopecia, including but not limited to alopecia areata, male pattern baldness, and/or alopecia capitis totalis. Antagonists of Claudin-23 can be used to prevent unwanted growth of hair.

Conditions of the gastrointestinal system also are treatable with Claudin-23 agonists of the invention, compositions or combination therapies, including coeliac disease. In addition, the compounds, compositions and combination therapies of the invention are used to treat Crohn's disease; ulcerative colitis; and ulcers, including gastric and duodenal ulcers.

Also provided herein are methods for using Claudin-23 agonists of the invention, compositions or combination therapies to treat various hematologic and oncologic disorders. For example, Claudin-23 agonists of the invention are used to treat various forms of cancer, including acute myelogenous leukemia, Epstein-Barr virus-positive nasopharyngeal carcinoma, glioma, colon, stomach, prostate, renal cell, cervical and ovarian cancers, lung cancer (SCLC and NSCLC), including cancer-associated cachexia, fatigue, asthenia, paraneoplastic syndrome of cachexia and hypercalcemia. Additional diseases treatable with the subject Claudin-23 agonists of the invention, compositions or combination therapies are solid tumors, including sarcoma, osteosarcoma, and carcinomas such as adenocarcinoma (for example, breast cancer) and squamous cell carcinoma. In addition, the subject compounds, compositions or combination therapies are useful for treating leukemia, including acute myelogenous leukemia, chronic or acute lymphoblastic leukemia and hairy cell leukemia. Other malignancies with invasive metastatic potential can be treated with the Claudin-23 agonist compounds, compositions and combination therapies, including multiple myeloma.

Administration of Claudin Polypeptides, Antagonists, or Agonists Thereof

This invention provides compounds, compositions, and methods for treating a subject, such as a mammalian or a human subject, who is suffering from a medical disorder, and in particular a human Claudin-23-mediated disorder. Such human Claudin-23-mediated disorders include conditions caused (directly or indirectly) or exacerbated by binding between human Claudin-23 and a binding partner. For purposes of this disclosure, the terms "illness," "disease," "medical condition," "abnormal condition" and the like are used interchangeably with the term "medical disorder." The terms "treat", "treating", and "treatment" used herein includes curative, preventative (e.g., prophylactic) and palliative or ameliorative treatment. For such therapeutic uses, Claudin polypeptides of the invention and fragments, Claudin-23 polynucleotides encoding the Claudin polypeptides of the invention, and/or agonists or antagonists of a Claudin-23 polypeptide such as antibodies can be administered to the subject in need through well-known means. Compositions of the invention can contain a polypeptide in any form described herein, such as native polypeptides, variants, derivatives, oligomers, and biologically active fragments. In particular embodiments, the composition comprises a soluble polypeptide or an oligomer comprising soluble Claudin polypeptides of the invention.

Therapeutically Effective Amount. In practicing the method of treatment or use of the invention, a therapeutically effective amount of a therapeutic agent of the invention is administered to a subject having a condition to be treated, preferably to treat or ameliorate diseases associated with the activity of a human Claudin-23 polypeptide. "Therapeutic agent" includes, without limitation, any of the Claudin polypeptides of the invention, fragments, and variants; polynucleotides encoding the Claudin polypeptides of the invention, fragments, and variants; agonists or antagonists of the Claudin polypeptides of the invention such as antibodies; Claudin-23 polypeptide binding partners; complexes formed from the Claudin polypeptides of the invention, fragments, variants, and binding partners, and the like. As used herein, the term "therapeutically effective amount" means the total amount of each therapeutic agent or other active component of the pharmaceutical composition or method that is sufficient to show a meaningful subject benefit, i.e., treatment, healing, prevention or amelioration of the relevant medical condition, or an increase in rate of treatment, healing, prevention or amelioration of such conditions. When applied to an individual therapeutic agent or active ingredient, administered alone, the term refers to that ingredient alone. When applied to a combination, the term refers to combined amounts of the ingredients that result in the therapeutic effect, whether administered in combination, serially or simultaneously. As used herein, the phrase "administering a therapeutically effective amount" of a therapeutic agent means that the subject is treated with said therapeutic agent in an amount and for a time sufficient to induce an improvement, and preferably a sustained improvement, in at least one indicator that reflects the severity of the disorder. An improvement is considered "sustained" if the subject exhibits the improvement on at least two occasions separated by one or more weeks. The degree of improvement is determined based on signs or symptoms, and determinations may also employ questionnaires that are administered to the subject, such as quality-of-life questionnaires. Various indicators that reflect the extent of the subject's illness may be assessed for determining whether the amount and time of the treatment is sufficient. The baseline value for the chosen indicator or indicators is established by examination of the subject prior to administration of the first dose of the therapeutic agent. Typically, the baseline examination is done within about 60 days of administering the first dose. If the therapeutic agent is being administered to treat acute symptoms, the first dose is administered as soon as practically possible after the injury has occurred. Improvement is induced by administering a therapeutic agent of the invention until the subject manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions. For injuries or acute conditions, a single dose may be sufficient. Although the extent of the subject's illness after treatment may appear improved according to one or more indicators, treatment may be continued indefinitely at the same level or at a reduced dose or frequency. Once treatment has been reduced or discontinued, it later may be resumed at the original level if symptoms should reappear.

Dosing. One skilled in the pertinent art will recognize that suitable dosages will vary, depending upon such factors as the nature and severity of the disorder to be treated, the subject's body weight, age, general condition, and prior illnesses and/or treatments, and the route of administration. Preliminary doses can be determined according to animal tests, and the scaling of dosages for human administration is performed according to art-accepted practices such as standard dosing trials. For example, the therapeutically effective dose can be estimated initially from cell culture assays. The dosage will depend on the specific activity of the compound and can be readily determined by routine experimentation. A dose may be formulated in animal models to achieve a circulating plasma concentration range that includes the $IC_{50}$ (i.e., the concentration of the test compound which achieves a half-maximal inhibition of symptoms) as determined in cell culture, while minimizing toxicities. Such information can be used to more accurately determine useful doses in humans. Ultimately, the attending physician will decide the amount of a therapeutic agent of the invention with which to treat each individual subject. Initially, the attending physician will administer low doses of a therapeutic agent of the invention and observe the subject's response. Larger doses of a therapeutic agent of the invention may be administered until the optimal therapeutic effect is obtained for the subject, and at that point the dosage is not increased further. It is contemplated that the various pharmaceutical compositions used to practice the method of the invention should contain about 0.01 ng to about 100 mg (or about 0.1 ng to about 10 mg, or about 0.1 microgram to about 1 mg) of a therapeutic agent of the invention per kg body weight. In one embodiment of the invention, Claudin polypeptides of the invention or antagonists are administered one time per week to treat the various medical disorders disclosed herein, in another embodiment is administered at least two times per week, and in another embodiment is administered at least three times per week. If injected, the effective amount of a therapeutic agent of the invention per adult dose ranges from 1–20 mg/m$^2$, and in one embodiment is about 5–12 mg/m$^2$. Alternatively, a flat dose may be administered, whose amount may range from 5–100 mg/dose. Exemplary dose ranges for a flat dose to be administered by subcutaneous injection are 5–25 mg/dose, 25–50 mg/dose and 50–100 mg/dose. In one embodiment of the invention, the various indications described below are treated by administering a preparation acceptable for injection containing a therapeutic agent of the invention at 25 mg/dose, or alternatively, containing 50 mg per dose. The 25 mg or 50 mg dose may be administered repeatedly, particularly for chronic conditions. If a route of administration other than injection is used, the dose is appropriately adjusted in accord with standard medical practices. In many instances, an improvement in a subject's condition will be obtained by injecting a dose of about 25 mg of a therapeutic agent of the invention one to three times per week over a period of at least three weeks, or a dose of 50 mg of a therapeutic agent of the invention one or two times per week for at least three weeks, though treatment for longer periods may be necessary to induce the desired degree of improvement. For incurable chronic conditions, the regimen may be continued indefinitely, with adjustments being made to dose and frequency if such are deemed necessary by the subject's physician. The foregoing doses are examples for an adult subject who is a person who is 18 years of age or older. For pediatric subjects (age 4–17), a suitable regimen involves the subcutaneous injection of 0.4 mg/kg, up to a maximum dose of 25 mg of a therapeutic agent of the invention, administered by subcutaneous injection one or more times per week. If an antibody against a Claudin-23 polypeptide is used as a Claudin-23 polypeptide antagonist, a typical dose range is 0.1 to 20 mg/kg, and in one embodiment is 1–10 mg/kg. Another dose range for an anti-Claudin-23 polypeptide antibody is 0.75 to 7.5 mg/kg of body weight. Humanized antibodies are antibodies in which only the antigen-binding portion of the antibody molecule is derived from a non-human source. Such antibodies may be injected or administered intravenously.

Formulations. Compositions comprising an effective amount of a Claudin-23 polypeptide of the invention (from whatever source derived, including without limitation from recombinant and non-recombinant sources), in combination with other components such as a physiologically acceptable diluent, carrier, or excipient, are provided herein. The term "pharmaceutically acceptable" means a non-toxic material that does not interfere with the effectiveness of the biological activity of the active ingredient(s). Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in Remington's Pharmaceutical Sciences, 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, and the like, or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference. Such compositions will influence the physical state, solubility, stability, rate of in vivo release, and rate of in vivo clearance, and are thus chosen according to the intended application, so that the characteristics of the carrier will depend on the selected route of administration. In one embodiment of the invention, sustained-release forms of Claudin polypeptides of the invention are used. Sustained-release forms suitable for use in the disclosed methods include, but are not limited to, Claudin polypeptides of the invention that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

Combinations of Therapeutic Compounds. A Claudin-23 polypeptide of the invention may be active in multimers (e.g., heterodimers or homodimers) or complexes with itself or other polypeptides. As a result, pharmaceutical compositions of the invention may comprise a polypeptide of the invention in such multimeric or complexed form. The pharmaceutical composition of the invention may be in the form of a complex of the polypeptide(s) of invention along with polypeptide or peptide antigens. The invention further includes the administration of Claudin polypeptides of the invention or antagonists concurrently with one or more other drugs that are administered to the same subject in combination with the Claudin polypeptides of the invention or antagonists, each drug being administered according to a regimen suitable for that medicament. "Concurrent administration" encompasses simultaneous or sequential treatment with the components of the combination, as well as regimens in which the drugs are alternated, or wherein one component is administered long-term and the other(s) are administered intermittently. Components may be administered in the same or in separate compositions, and by the same or different routes of administration. Examples of components that may be included in the pharmaceutical composition of the invention are: cytokines, lymphokines, or other hematopoietic factors such as M-CSF, GM-CSF, TNF, IL-1, IL-2, IL-3, IL4, IL-5, IL-6, IL-7, IL-8, IL-9, IL-10, IL-11, IL-12, IL-13, IL-14, IL-15, IL-17, IL-18, IFN, G-CSF, thrombopoietin, stem cell factor, and erythropoietin. The pharmaceutical composition may further contain other agents which either enhance the activity of the polypeptide or compliment its activity or use in treatment. Such additional factors and/or agents may be included in the pharmaceutical composition to produce a synergistic effect with polypeptide of the invention, or to minimize side effects. Conversely, a Claudin-23 polypeptide or antagonist of the invention may be included in formulations of the particular cytokine, lymphokine, other hematopoietic factor, thrombolytic or antithrombotic factor, or anti-inflammatory agent to minimize side effects of the cytokine, lymphokine, other hematopoietic factor, thrombolytic or anti-thrombotic factor, or anti-inflammatory agent. Additional examples of drugs to be administered concurrently include, but are not limited to, antivirals, antibiotics, analgesics, corticosteroids, antagonists of inflammatory cytokines, non-steroidal anti-inflammatories, pentoxifylline, thalidomide, and disease-modifying antirheumatic drugs (DMARDs) such as azathioprine, cyclophosphamide, cyclosporine, hydroxychloroquine sulfate, methotrexate, leflunomide, minocycline, penicillamine, sulfasalazine and gold compounds such as oral gold, gold sodium thiomalate, and aurothioglucose. Additionally, Claudin polypeptides of the invention or antagonists may be combined with a second Claudin-23 polypeptide/antagonist, including an antibody against a Claudin-23 polypeptide, or a Claudin-23 polypeptide-derived peptide that acts as a competitive inhibitor of a native Claudin-23 polypeptide.

Routes of Administration. Any efficacious route of administration may be used to therapeutically administer Claudin polypeptides of the invention or antagonists thereof, including those compositions comprising polynucleotides. Parenteral administration includes injection, for example, via intra-articular, intravenous, intramuscular, intralesional, intraperitoneal or subcutaneous routes by bolus injection or by continuous infusion, and also includes localized administration, e.g., at a site of disease or injury. Other suitable means of administration include sustained release from implants; aerosol inhalation and/or insufflation; eyedrops; vaginal or rectal suppositories; buccal preparations; oral preparations, including pills, syrups, lozenges or chewing gum; and topical preparations such as lotions, gels, sprays, ointments or other suitable techniques. Alternatively, polypeptideaceous Claudin-23 molecules of the invention or antagonists may be administered by implanting cultured cells that express a polypeptide, for example, by implanting cells that express Claudin polypeptides of the invention or antagonists. Cells may also be cultured ex vivo in the presence of polypeptides of the invention in order to proliferate or to produce a desired effect on or activity in such cells. Treated cells can then be introduced in vivo for therapeutic purposes. In another embodiment, the subject's own cells are induced to produce Claudin polypeptides of the invention or antagonists by transfection in vivo or ex vivo with a DNA that encodes Claudin polypeptides of the invention or antagonists. This DNA can be introduced into the subject's cells, for example, by injecting naked DNA or liposome-encapsulated DNA that encodes Claudin polypeptides of the invention or antagonists, or by other means of transfection. Polynucleotides of the invention may also be administered to subjects by other known methods for introduction of polynucleotide into a cell or organism (including, without limitation, in the form of viral vectors or naked DNA). When Claudin polypeptides of the invention or antagonists are administered in combination with one or more other biologically active compounds, these may be administered by the same or by different routes, and may be administered simultaneously, separately or sequentially.

Oral Administration. When a therapeutically effective amount of polypeptide of the invention is administered orally, polypeptide of the invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% a polypeptide of the invention, and typically from about 25 to 90% polypeptide of the invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of polypeptide of the invention, and typically from about 1 to 50% a polypeptide of the invention.

Intravenous Administration. When a therapeutically effective amount of polypeptide of the invention is administered by intravenous, cutaneous or subcutaneous injection, polypeptide of the invention will be in the form of a pyrogen-free, parenterally acceptable aqueous solution. The preparation of such parenterally acceptable polypeptide solutions, having due regard to pH, isotonicity, stability, and the like, is within the skill in the art. A pharmaceutical composition for intravenous, cutaneous, or subcutaneous injection should contain, in addition to polypeptide of the invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the invention may also contain stabilizers, preservatives, buffers, antioxidants, or other additives known to those of skill in the art. The duration of intravenous therapy using the pharmaceutical composition of the invention will vary, depending on the severity of the disease being treated and the condition and potential idiosyncratic response of each individual subject. It is contemplated that the duration of each application of the polypeptide of the invention will be in the range of 12 to 24 hours of continuous intravenous administration. Ultimately the attending physician will decide on the appropriate duration of intravenous therapy using the pharmaceutical composition of the invention.

Bone and Tissue Administration. For compositions of the invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a polypeptide of the invention, which may also optionally be included in the composition, as described above, may alternatively or additionally, be administered simultaneously or sequentially with the composition in the methods of the invention. Typically for bone and/or cartilage formation, the composition would include a matrix capable of delivering the polypeptide-containing composition to the site of bone and/or cartilage damage, providing a structure for the developing bone and cartilage and optimally capable of being resorbed into the body. Such matrices may be formed of materials presently in use for other implanted medical applications. The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well defined, such as bone or dermal collagen. Further matrices are comprised of pure polypeptides or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. One embodiment is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the polypeptide compositions from disassociating from the matrix. A typical family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most common being cationic salts of carboxymethylcellulose (CMC). Other sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, typically 1–10 wt % based on total formulation weight, which represents the amount necessary to prevent desorbtion of the polypeptide from the polymer matrix and to provide appropriate handling of the composition, yet not so much that the progenitor cells are prevented from infiltrating the matrix, thereby providing the polypeptide the opportunity to assist the osteogenic activity of the progenitor cells. In further compositions, polypeptides of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF). The therapeutic compositions are also presently valuable for veterinary applications. Particularly domestic animals and thoroughbred horses, in addition to humans, are desired subjects for such treatment with polypeptides of the invention. The dosage regimen of a polypeptide-containing pharmaceutical composition to be used in tissue regeneration will be determined by the attending physician considering various factors which modify the action of the polypeptides, e.g., amount of tissue weight desired to be formed, the site of damage, the condition of the damaged tissue, the size of a wound, type of damaged tissue (e.g., bone), the subject's age, sex, and diet, the severity of any infection, time of administration and other clinical factors. The dosage may vary with the type of matrix used in the reconstitution and with inclusion of other polypeptides in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Veterinary Uses. In addition to human subjects, Claudin polypeptides of the invention and antagonists are useful in the treatment of disease conditions in non-human animals, such as pets (dogs, cats, birds, primates, etc.), domestic farm animals (horses cattle, sheep, pigs, birds, etc.), or any animal that suffers from a TNFα-mediated inflammatory or arthritic condition. In such instances, an appropriate dose may be determined according to the animal's body weight. For example, a dose of 0.2–1 mg/kg may be used. Alternatively, the dose is determined according to the animal's surface area, an exemplary dose ranging from 0.1–20 mg/m$^2$, and in one embodiment, from 5–12 mg/m$^2$. For small animals, such as dogs or cats, a suitable dose is 0.4 mg/kg. In one embodiment, Claudin polypeptides of the invention or antagonists (preferably constructed from genes derived from the same species as the subject), is administered by injection or other suitable route one or more times per week until the animal's condition is improved, or it may be administered indefinitely.

Manufacture of Medicaments. The invention also relates to the use Claudin polypeptides of the invention, fragments, and variants; polynucleotides encoding the Claudin polypeptides of the invention, fragments, and variants; agonists or antagonists of the Claudin polypeptides of the invention such as antibodies; Claudin-23 polypeptide binding partners; complexes formed from the Claudin polypeptides of the invention, fragments, variants, and binding partners, etc, in the manufacture of a medicament for the prevention or therapeutic treatment of each medical disorder disclosed herein.

EXAMPLES

The following examples are intended to illustrate particular embodiments and not to limit the scope of the invention.

Example 1

Identification of Claudin-23

Mice deficient in RIP4 expression were analyzed (Holland et al., 2002, *Current Biology* 12: 1424–1428, which is incorporated by reference in its entirety herein). The protein kinase RIP4 is sometimes referred to as Death-Associated Kinase containing Ankyrin Repeats (DAKAR), Feldspar, protein kinase C-associated kinase or PKK (Chen et al., 2001, *J Biol Chem* 276: 21737–21744), or DIK (Bähr et al., 2000, *J Biol Chem* 275: 36350–36357). The phenotype observed for RIP4-deficient embryos shows some similarities to that reported for IKKalpha knockout animals (Takeda, K., et al., *Science,* 284:313. 1999; Hu, Y., et al., *Science,* 284:316, 1999; Hu, Y., et al., *Nature,* 410:710, 2001), but is distinct in certain respects. Unlike IKKalpha which has a role in the inflammation-related NFkB signaling pathway, it is suspected that the role of RIP4 in skin development is in regulating morphogenetic events, particularly keratinocyte proliferation and differentiation, not in regulating inflammatory responses. RIP4-deficient mice show variety of defects in cells derived from the keratinocyte lineage: fusion of all external orifices and of the esophagus; fusion of the interdigital epithelium; poor development of vibrissae; and replacement of the cornified layers of the skin by a thick layer of flattened, parakeratotic cells. RIP4 appears to act cell-autonomously within the keratinocyte cell lineage, because RIP4-deficient skin fails to differentiate when grafted onto a normal host.

RNA preparations were prepared from the skin of wild-type mouse embryos and also from the skin of embryos deficient in RIP4, using the RNeasy kit (Qiagen) followed by treatment with DNAse I (Ambion Inc.; Austin, Tex.) to eliminate residual chromosomal DNA contaminations. The RNA was labeled and hybridized to Affymetrix (Santa Clara, Calif.) U74Av2 chips according to the manufacturer's protocol. RESOLVER software (Rosetta Inpharmatics, a subsidiary of Merck & Co.; Whitehouse Station, N.J.) was used to analyze the data from the DNA array chips. RESOLVER analysis of the U74Av2 chips revealed a 4–8 fold down-regulation of a polynucleotide defined as IC2a-34134_at in RIP4-deficient mouse embryos. The down-regulated polynucleotide was homologous to a Genbank database entry, AK009330, for a putative mouse gene (SEQ ID NO:7). The down-regulated polynucleotide (SEQ ID NO:7) was used in a TBLASTN search of human genomic DNA sequences. The search revealed a similar human nucleic acid molecule, which is referred to herein as a human Claudin-23 polynucleotide (SEQ ID NO:5), present as a single exon in chromosome 8. The predicted polypeptide sequence of human Claudin-23 is provided in SEQ ID NO:6. Accordingly, the murine sequence first identified as down-regulated in RIP4-deficient mice is a homolog of human Claudin-23 and is referred to herein as a murine Claudin-23. Human Claudin-23 is notable for possession of the four characteristic transmembrane domains of Claudin polypeptides, the first of which spans from about amino acid 5 to about 27 of SEQ ID NO:6. This is consistent with other Claudin family members in that the first transmembrane domain is inserted into the cell membrane with the very N-terminal end of the Claudin polypeptide located inside the cell. Human Claudin-23's second TM domain comprises from about amino acids 77 to 99 of SEQ ID NO:6, a third TM domain comprises from about amino acids 112 to 134 of SEQ ID NO:6, and a fourth TM domain comprises from about amino acids 160 to 182 of SEQ ID NO:6. Based on the alignments with other family members and by reference to FIG. 1 of Morita et al. These predicted locations for the four TM domains of Human Claudin-23 places the first extracellular loop of Human Claudin-23 as beginning approximately around amino acid 28 to amino acid 31 of SEQ ID NO:6 and extending to approximately amino acid 76 of SEQ ID NO:6, and the second extracellular loop of Human Claudin-23 as beginning approximately around amino acid 135 to amino acid 138 of SEQ ID NO:6 and extending to approximately amino acid 159 of SEQ ID NO:6. The intracellular sequence between the second and third TM domains begins at approximately amino acid 100 to 103 of SEQ ID NO:6 and extends to approximately amino acid 111 of SEQ ID NO:6. The cytoplasmic tail domain of Human Claudin-23 begins approximately around amino acid 182 to amino acid 184 (e.g., about amino acid 183) of SEQ ID NO:6 and extends to the predicted C-terminus of SEQ ID NO:6 at amino acid 292.

The amino acid sequence of human Claudin-23 (SEQ ID NO:6) was compared with the amino acid sequences of other Claudin family members such as Claudin-1 (SEQ ID NO:1), Claudin4 (SEQ ID NO:2), Claudin-6 (SEQ ID NO:3), and Claudin-7 (SEQ ID NO:4), as shown in Table 1 below. This comparison used the GCG "pretty" multiple sequence alignment program, with amino acid similarity scoring matrix=blosum62, gap creation penalty=8, and gap extension penalty=2. The alignment of these sequences shown in Table 1 shows capitalized consensus residues that are identical among at least four of the amino acid sequences in the alignment, and the numbering of positions in the alignment is that of each residue's position in the human Claudin-23 amino acid sequence (SEQ ID NO:6). Embodiments of the invention include Claudin polypeptides and fragments of Claudin polypeptides comprising altered amino acid sequences. Altered Claudin-23 polypeptide sequences share at least 30%. or at least 40%, or at least 50%, or at least 55%, or at least 60%, or at least 65%, or at least 70%, or at least 75%, or at least 80%, or at least 85%, or at least 90%, or at least 95%, or at least 97.5%, or at least 99%, or at least 99.5% amino acid identity with a Claudin amino acid sequence shown in Table 1.

Amino acid substitutions and other alterations (deletions, insertions, and the like) to the Claudin polypeptides of the invention are predicted to be more likely to alter or disrupt Claudin polypeptide activities if they result in changes to the capitalized residues shown in Table 1, and particularly if those changes do not substitute a residue present in another Claudin polypeptide at that conserved position. Conversely, if a change is made to a Claudin amino acid sequence resulting in substitution of one or more Table 1 consensus sequence residues for the Claudin polypeptide residue at that conserved position, it is less likely that such an alteration will affect Claudin polypeptide function. For example, the consensus residue at position 40 in Table 1 is isoleucine in four of the five Claudin molecules, whereas human Claudin-23 has a proline at this position. Substitution of isoleucine or a chemically similar residues such as valine or one of the aliphatic amino acids at that position is considered less likely to alter the function of a Claudin-23 polypeptide than substitution of charged residues such as lysine or arginine. In addition to the substitution of isoleucine for proline at position 40 of SEQ ID NO:6 (symbolized as 40P—>I), the following additional variants of the amino acid sequence of SEQ ID NO:6 are expected to retain Claudin-23 polypeptide activity, based on substitution of an amino acid present in other Claudins at the corresponding position: 16C—>L; 18L—>W; 72F—>L; 78L—>Q; 121L—>F; and 176 S—>L:

Further types of variations that can be made to the Claudin-23 amino acid sequences of SEQ ID NO:6 and SEQ ID NO:8, such that the variants are expected to retain Claudin-23 polypeptide activity, are conservative changes to residues throughout the polypeptide. Conservative changes are those that substitute for a given amino acid an amino acid of a similar chemical type; amino acids can be grouped into similar chemical types as follows: aliphatic amino acids (alanine, glycine, isoleucine, leucine, proline, valine); aromatic amino acids (phenylalanine, tryptophan, tyrosine); amino acids with hydroxyl side chains (hydroxyproline, serine, threonine); sulfur-containing amino acids (cysteine, methionine); amino acids with amide side chains (asparagine, glutamine); amino acids with acidic side chains (aspartic acid, glutamic acid); and amino acids with basic side chains (arginine, histidine, lysine). Examples of conservative substitutions in SEQ ID NO:6 are: 37L—>G; 41V—>I; 46Y—>W; 58S—>T; 160L—>I; and 164Y—>W.

TABLE 1

Protein (SEQ ID NO)

```
                    1                                                      49
hClaudin4   (2) MAsmGlQvmGiaLAvLGWlavmlccAlPmWrvtafiGsnIVtsQtiweGL
hClaudin6   (3) MAsaGmQiLGvvLtlLGWvnglvscAlPmWkvtafiGnsIVvaQvvweGL
hClaudin1   (1) MAnaGlQlLGfiLAfLGWigaivstAlPqWriysyaGdnIVtaQamyeGL
hClaudin7   (4) MAnsGlQlLGfsmAlLGWvglvactAiPqWqmssyaGdnIitaQamykGL
hClaudin23  (6) MrtpvvmtLGmvLApcGlllnltgtlaPgWrlvkgflnqpVdve.lyqGL
    Consensus   MA--G-Q-LG--LA-LGW-------A-P-W------G--IV--Q----GL 50                                                     99
hClaudin4   (2) WMnCVvQSTGqmqCKvyDSlLaL.pqdLQAaRALviisiivaalgvllsv
hClaudin6   (3) WMsCVvQSTGqmqCKvyDSlLaL.pqdLQAaRALcViallvalfgllvyl
hClaudin1   (1) WMsCVsQSTGqiqCKvfDSlLnL.sstLQAtRALmVvgillgviaifvat
hClaudin7   (4) WMdCVtQSTGmmsCKmyDSvLaL.ssaLQAtRALmVvslvlgflamfvat
hClaudin23  (6) WdmCReQSsrereCgqtDqwgyfeaqpvlvaRALmVtslaatvlglllas
    Consensus   WM-CV-QSTG---CK--DS-L-L----LQA-RAL-V--------------

100                                                    144
hClaudin4   (2) vGgKCtnCl.eDesaKaktmivaGvvFllAGLmvivpvsWtaHniiqdFY
hClaudin6   (3) aGaKCttCv.eekdsKarlvltsGivFvisGvltLipvcWtaHavirdFY
hClaudin1   (1) vGmKCmkCledDevqKmrmavigGaiFllAGLaiLvataWygnrivqeFY
hClaudin7   (4) mGmKCtrCggdDkvkKariamggGiiFivAGLaaLvacsWygHqivtdFY
hClaudin23  (6) lGvrC....wqDepnfv.laglsGvvlfvAGLlgLipvsWynHflgdrdv
    Consensus   -G-KC--C---D---K-------G--F--AGL--L----W--H-----FY 145                                                    194
hClaudin4   (2) nPlvasgqkrEmGasLyvGWAaSgLlLLGGgLLcCn.CP...prtdkpYs
hClaudin6   (3) nPlvaeaqkrElGasLylGWAaSgLlLLGGgLLcCt.CPsggsqgpshYm
hClaudin1   (1) dPmtpvnaryEfGqaLftGWAaasLcLLGGaLLcCs.CP....rkttsYp
hClaudin7   (4) nPliptnikyEfGpaifiGWAgsSaLviLGGaLLsCs.CP..gneskagYr
hClaudin23  (6) lPapaspvtvqvsysLvlGylgScLlLLGGfsLalsfaPwcdercrrrrk
    Consensus   -P--------E-G--L--GWA-S-L-LLGG-LL-C--CP---------Y-

195                                                    244
hClaudin4   (2) akysa...arsaaas nYv------------------------------
hClaudin6   (3) arystsapaisrgps eYptknyv-------------------------
hClaudin1   (1) tprpypkpapssg.k.dYv------------------------------
hClaudin7   (4) aprsypk..snss.k.eYv------------------------------
hClaudin23  (6) gpsagprrssvstiqvewpepdlapaikyysdgqhrpppaqhrkpkpkpk
    Concensus   ----------------Y--------------------------------

245                                                    292
hClaudin23  (6) vgfpmprprpkaytnsvdvldgegwesqdapscsthpcdsslpcdsdl
```

Additional types of variations that can be made to the Claudin-23 amino acid sequences of SEQ ID NO:6 and SEQ ID NO:8 are changes to the transmembrane domains of these polypeptides. Substitutions that preserve the hydrophobic nature of these transmembrane domains by substituting for transmembrane residues uncharged amino acids, and particularly aliphatic or aromatic amino acids, are expected to result in variants that retain Claudin-23 polypeptide activity. Insertions of 1 through about 10 amino acids, or deletions of 1 through about 8 amino acids, for each transmembrane domain, where such insertions or deletions preserve the hydrophobic nature of these transmembrane domains, are also within the scope of the invention. The overall topological structure of such Claudin-23 variants can be predicted using a program such as the TMHMM (TransMembrane Hidden Markov Model) application available on the internet from the Center for Biological Sequence Analysis of the Technical University of Denmark (cbs.dtu.dk/services/TM-HMM). Examples of such insertions or deletions that retain the four transmembrane structure of Claudin-23 are: insertion of five leucine residues between amino acids 15 and 16 of SEQ ID NO:6; insertion of ten leucine residues between amino acids 15 and 16 of SEQ ID NO:6; deletion of amino acids 19 through 23 of SEQ ID NO:6; and deletion of amino acid 16 and amino acids 19 through 25 of SEQ ID NO:6. For the previous examples of Claudin-23 transmembrane domain variants, TMHMM analysis clearly indicated the presence of four transmembrane domains having the same overall topology as the Claudin-23 polypeptide of SEQ ID NO:6. Further, TMHMM analysis can indicate when a variant of a Claudin-23 polypeptide is not expected to retain the four transmembrane structure: for example, deletion of amino acids 11 through 12, 16, and 19 through 25 of SEQ ID NO:6 produced a variant that was predicted by TMHMM analysis to lack the most N-terminal transmembrane domain.

Polynucleotide sequences encoding human Claudin-23 map to human chromosome 8p23.1. Polynucleotides encoding Claudin polypeptides of the invention can be used to analyze genetic abnormalities associated with these chromosomal regions, for example, enabling one of skill in the art to identify subjects in which chromosomal regions comprising Claudin-encoding sequences are rearranged or deleted. There is also substantial utility in polynucleotides that can be used to confirm or to eliminate a particular genetic locus as a genetic factor for a kindred presenting with a hereditary disease. Human genetic disorders that have been mapped to the same chromosomal region as Claudin-23 include Keratolytic Winter Erythema (KWE) and Diamond-Blackfan Anemia 2 (DBA2). Claudin-23 polynucleotides are useful for more precisely mapping these genetic disorders within the p23 region of chromosome 8. Also, Claudin-23 is a candidate for being the gene implicated in the skin disorder KWE, because changes in Claudin-23 expression are associated with the skin disorders observed in RIP4-deficient mice as described above. Further, KWE is an autosomal dominant disorder; if Claudin-23 was the gene responsible for KWE, then KWE could be caused by dominant-negative forms of Claudin-23, with loss-of-function mutations of Claudin-23 being recessive lethal.

Example 2

Expression of Human Claudin-23 Transcripts and Proteins

The expression of murine Claudin-23 in different tissues was detected using RT-PCR. PCR was carried out as follows: 5' (sense) oligo sequence was AAG AGG CTA CGC AGG ATG CGG ACG CC (SEQ ID NO:9) and the 3' (antisense) oligo was CTG TCT ACA GGT CGG AGT CAC AGG GCA (SEQ ID NO:10) were incubated according to standard protocols with dNTP's, Clontech Mouse multiple tissue cDNAs (heart, brain, spleen, lung, liver, skeletal muscle, kidney, testis, E7, E11, E15, and E17), and Applied Biosystems Amplitaq as the polymerase. PCR cycling parameters were: denature at 95 degrees C. for 5 minutes followed by 35 cycles of (a) denaturation at 95 degrees C. for 1 minute; (b) annealing at 65 degrees C. for 1 minute; and (c) primer extension at 72 degrees C. for 2 minutes.

Claudin-23 transcripts were detected in the following murine tissues: brain, lung, and testis. Claudin-23 was also detected in embryos at stages E15 and E17. In addition, as described above, the skin showed differing rates of expression between normal and RIP4-deficient mice. In addition, human Claudin-23 was detected in Dendritic cells (DC) by standard RT-PCR. Human Claudin-23 was detected in sorted CD1b/c+ DC RNA from a normal Flt3-L treated donor. Claudin-23 was also weakly detected in $CD8^+$ T cells and $CD4^+$ T cells.

Example 3

Monoclonal Antibodies That Bind Polypeptides of the Invention

This example illustrates a method for preparing monoclonal antibodies that bind Claudin-23 polypeptides of the invention. Other conventional techniques may be used, such as those described in U.S. Pat. No. 4,411,993. Suitable immunogens that may be employed in generating such antibodies include, but are not limited to, purified Claudin-23 polypeptide of the invention, an immunogenic fragment thereof, and cells expressing high levels of said Claudin-23 polypeptide or an immunogenic fragment thereof. DNA encoding a Claudin-23 polypeptide of the invention can also be used as an immunogen, for example, as reviewed by Pardoll and Beckerleg in *Immunity* 3: 165, 1995.

Rodents (BALB/c mice or Lewis rats, for example) are immunized with Claudin-23 polypeptide immunogen emulsified in an adjuvant (such as complete or incomplete Freund's adjuvant, alum, or another adjuvant, such as Ribi adjuvant R700 (Ribi, Hamilton, and injected in amounts ranging from 10–100 micrograms subcutaneously or intraperitoneally. DNA may be given intradermally (Raz et al., 1994, *Proc. Nail. Acad. Sci. USA* 91: 9519) or intamuscularly (Wang et al., 1993, *Proc. Natl. Acad. Sci. USA* 90: 4156); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision to test for Claudin-23 polypeptide-specific antibodies by dot-blot assay, ELISA (enzyme-linked immunosorbent assay), immunoprecipitation, or other suitable assays, such as FACS analysis of inhibition of binding of Claudin-23 polypeptide of the invention to a Claudin-23 polypeptide binding partner. Following detection of an appropriate antibody titer, positive animals are provided one last intravenous injection of Claudin-23 polypeptide of the invention in saline. Three to four days later, the animals are sacrificed, and spleen cells are harvested and fused to a murine myeloma cell line, e.g., NS1 or preferably P3X63Ag8.653 (ATCC CRL-1580). These cell fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells may be screened by ELISA for reactivity against purified Claudin-23 polypeptide of the invention by adaptations of the techniques disclosed in Engvall et al., (*Immunochem.* 8: 871, 1971) and in U.S. Pat. No. 4,703,004. A preferred screening technique is the antibody capture technique described in Beckmann et al., (*J. Immunol.* 144: 4212, 1990). Positive hybridoma cells can be injected intraperitoneally into syngeneic rodents to produce ascites containing high concentrations (for example, greater than 1 milligram per milliliter) of anti-Claudin-23 polypeptide monoclonal antibodies. Alternatively, hybridoma cells can be grown in vitro in flasks or roller bottles by various techniques. Monoclonal antibodies can be purified by ammonium sulfate precipitation, followed by gel exclusion chromatography. Alternatively, affinity chromatography based upon binding of antibody to protein A or protein G can also be used, as can affinity chromatography based upon binding to the Claudin-23 polypeptide of the invention.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Sequences Presented in the Sequence Listing

| SEQ ID NO | Sequence Type | Description |
|---|---|---|
| SEQ ID NO: 1 | Amino acid | Human Claudin-1 |
| SEQ ID NO: 2 | Amino acid | Human Claudin-4 |
| SEQ ID NO: 3 | Amino acid | Human Claudin-6 |
| SEQ ID NO: 4 | Amino acid | Human Claudin-7 |
| SEQ ID NO: 5 | Nucleotide | Human Claudin-23 |
| SEQ ID NO: 6 | Amino acid | Human Claudin-23 |
| SEQ ID NO: 7 | Nucleotide | Murine Claudin-23 (GenBank AK009330) |
| SEQ ID NO: 8 | Amino acid | Murine Claudin-23 |
| SEQ ID NO: 9 | Nucleotide | Claudin-23 'sense' oligonucleotide primer |
| SEQ ID NO: 10 | Nucleotide | Claudin-23 'antisense' oligonucleotide primer |

What is claimed is:

1. A method for identifying an agent that modulates the polypeptide having SEQ ID NO: 6, comprising mixing a test agent with the said polypeptide and determining whether there is a change in the activity of the polypeptide in the presence of the test agent relative to the activity of the polypeptide in the absence of the test agent, wherein the change of the activity of the polypeptide comprises an assessment of transcription and/or translation of skin differentiation marker, thereby identifying an agent that modulates polypeptide activity.

2. The method of claim 1, wherein the test agent is selected from the group consisting of small molecules, peptides, and antibodies.

3. The method of claim 1, wherein the skin differentiation marker is selected from the group consisting of:
a) filaggrin,
b) profilaggrin,
c) involucrin, and
d) keratin markers.

* * * * *

SEQUENCE LISTING

<160> NUMBER OF SEQ ID NOS: 10

<210> SEQ ID NO 1
<211> LENGTH: 211
<212> TYPE: PRT
<213> ORGANISM: Homo sapiens

<400> SEQUENCE: 1

```
Met Ala Asn Ala Gly Leu Gln Leu Leu Gly Phe Ile Leu Ala Phe Leu
1               5                   10                  15

Gly Trp Ile Gly Ala Ile Val Ser Thr Ala Leu Pro Gln Trp Arg Ile
            20                  25                  30

Tyr Ser Tyr Ala Gly Asp Asn Ile Val Thr Ala Gln Ala Met Tyr Glu
        35                  40                  45

Gly Leu Trp Met Ser Cys Val Ser Gln Ser Thr Gly Gln Ile Gln Cys
    50                  55                  60

Lys Val Phe Asp Ser Leu Leu Asn Leu Ser Ser Thr Leu Gln Ala Thr
65                  70                  75                  80

Arg Ala Leu Met Val Val Gly Ile Leu Leu Gly Val Ile Ala Ile Phe
                85                  90                  95

Val Ala Thr Val Gly Met Lys Cys Met Lys Cys Leu Glu Asp Asp Glu
            100                 105                 110

Val Gln Lys Met Arg Met Ala Val Ile Gly Gly Ala Ile Phe Leu Leu
        115                 120                 125

Ala Gly Leu Ala Ile Leu Val Ala Thr Ala Trp Tyr Gly Asn Arg Ile
    130                 135                 140

Val Gln Glu Phe Tyr Asp Pro Met Thr Pro Val Asn Ala Arg Tyr Glu
145                 150                 155                 160

Phe Gly Gln Ala Leu Phe Thr Gly Trp Ala Ala Ala Ser Leu Cys Leu
                165                 170                 175

Leu Gly Gly Ala Leu Leu Cys Cys Ser Cys Pro Arg Lys Thr Thr Ser
            180                 185                 190

Tyr Pro Thr Pro Arg Pro Tyr Pro Lys Pro Ala Pro Ser Ser Gly Lys
        195                 200                 205

Asp Tyr Val
    210
```

<210> SEQ ID NO 2
<211> LENGTH: 209
<212> TYPE: PRT
<213> ORGANISM: Homo sapiens

<400> SEQUENCE: 2

```
Met Ala Ser Met Gly Leu Gln Val Met Gly Ile Ala Leu Ala Val Leu
1               5                   10                  15

Gly Trp Leu Ala Val Met Leu Cys Cys Ala Leu Pro Met Trp Arg Val
            20                  25                  30

Thr Ala Phe Ile Gly Ser Asn Ile Val Thr Ser Gln Thr Ile Trp Glu
        35                  40                  45

Gly Leu Trp Met Asn Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Val Ile Ile Ser Ile Ile Val Ala Ala Leu Gly Val Leu
                85                  90                  95
```

```
Leu Ser Val Val Gly Gly Lys Cys Thr Asn Cys Leu Glu Asp Glu Ser
            100                 105                 110

Ala Lys Ala Lys Thr Met Ile Val Ala Gly Val Val Phe Leu Leu Ala
            115                 120                 125

Gly Leu Met Val Ile Val Pro Val Ser Trp Thr Ala His Asn Ile Ile
            130                 135                 140

Gln Asp Phe Tyr Asn Pro Leu Val Ala Ser Gly Gln Lys Arg Glu Met
145                 150                 155                 160

Gly Ala Ser Leu Tyr Val Gly Trp Ala Ser Gly Leu Leu Leu
                165                 170                 175

Gly Gly Gly Leu Leu Cys Cys Asn Cys Pro Pro Arg Thr Asp Lys Pro
            180                 185                 190

Tyr Ser Ala Lys Tyr Ser Ala Ala Arg Ser Ala Ala Ser Asn Tyr
            195                 200                 205

Val

<210> SEQ ID NO 3
<211> LENGTH: 220
<212> TYPE: PRT
<213> ORGANISM: Homo sapiens

<400> SEQUENCE: 3

Met Ala Ser Ala Gly Met Gln Ile Leu Gly Val Val Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
            115                 120                 125

Gly Val Leu Thr Leu Ile Pro Val Cys Trp Thr Ala His Ala Val Ile
            130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190

Pro Ser His Tyr Met Ala Arg Tyr Ser Thr Ser Ala Pro Ala Ile Ser
            195                 200                 205

Arg Gly Pro Ser Glu Tyr Pro Thr Lys Asn Tyr Val
210                 215                 220

<210> SEQ ID NO 4
<211> LENGTH: 211
<212> TYPE: PRT
<213> ORGANISM: Homo sapiens
```

```
<400> SEQUENCE: 4

Met Ala Asn Ser Gly Leu Gln Leu Leu Gly Phe Ser Met Ala Leu Leu
1               5                   10                  15

Gly Trp Val Gly Leu Val Ala Cys Thr Ala Ile Pro Gln Trp Gln Met
            20                  25                  30

Ser Ser Tyr Ala Gly Asp Asn Ile Ile Thr Ala Gln Ala Met Tyr Lys
        35                  40                  45

Gly Leu Trp Met Asp Cys Val Thr Gln Ser Thr Gly Met Met Ser Cys
    50                  55                  60

Lys Met Tyr Asp Ser Val Leu Ala Leu Ser Ala Ala Leu Gln Ala Thr
65                  70                  75                  80

Arg Ala Leu Met Val Val Ser Leu Val Leu Gly Phe Leu Ala Met Phe
                85                  90                  95

Val Ala Thr Met Gly Met Lys Cys Thr Arg Cys Gly Gly Asp Asp Lys
            100                 105                 110

Val Lys Lys Ala Arg Ile Ala Met Gly Gly Gly Ile Ile Phe Ile Val
        115                 120                 125

Ala Gly Leu Ala Ala Leu Val Ala Cys Ser Trp Tyr Gly His Gln Ile
    130                 135                 140

Val Thr Asp Phe Tyr Asn Pro Leu Ile Pro Thr Asn Ile Lys Tyr Glu
145                 150                 155                 160

Phe Gly Pro Ala Ile Phe Ile Gly Trp Ala Gly Ser Ala Leu Val Ile
                165                 170                 175

Leu Gly Gly Ala Leu Leu Ser Cys Ser Cys Pro Gly Asn Glu Ser Lys
            180                 185                 190

Ala Gly Tyr Arg Ala Pro Arg Ser Tyr Pro Lys Ser Asn Ser Ser Lys
        195                 200                 205

Glu Tyr Val
    210

<210> SEQ ID NO 5
<211> LENGTH: 879
<212> TYPE: DNA
<213> ORGANISM: Homo sapiens

<400> SEQUENCE: 5
atgcggacgc cggtggtgat gacgctgggc atggtgttgg cgccctgcgg gctcctgctc    60
aacctgaccg gcaccctggc gcccggctgg cggctggtga agggcttcct gaaccagcca   120
gtggacgtgg agttgtacca gggcctgtgg gacatgtgtc gcgagcagag cagccgcgag   180
cgcgagtgcg gccagacgga ccagtggggc tacttcgagg cccagcccgt gctggtggcg   240
cgggcactca tggtcacctc gctggccgcc acggtcctgg ggcttctgct ggcgtcgctg   300
ggcgtgcgct gctggcagga cgagcccaac ttcgtgctgg cagggctctc gggcgtcgtg   360
ctcttcgtcg ctggcctcct cggcctcatc ccggtgtcct ggtacaacca cttcttgggg   420
gaccgcgacg tgctgcccgc cccggccagc ccggtcacgg tgcaggtcag ctacagcctg   480
gtcctgggct acctgggcag ctgcctcctg ctgctgggcg gcttctcgct ggcgctcagc   540
ttcgcgccct ggtgcgacga gcgttgtcgc cgccgccgca agggaccctc cgccgggcct   600
cgccgcagca gcgtcagcac catccaagtg gagtggcccg agcccgacct ggcgcccgcc   660
atcaagtact acagcgacgg ccagcaccga ccgccgcctg cccagcaccg caagcccaag   720
cccaagccca aggtcggctt ccccatgccg cggccgcggc ccaaggccta caccaactcg   780
```

```
gtggacgtcc tcgacgggga ggggtgggag tcccaggacg ctccctcgtg cagcacccac    840
ccctgcgaca gctcgctgcc ctgcgactcc gacctctag                          879
```

<210> SEQ ID NO 6
<211> LENGTH: 292
<212> TYPE: PRT
<213> ORGANISM: Homo sapiens

<400> SEQUENCE: 6

```
Met Arg Thr Pro Val Val Met Thr Leu Gly Met Val Leu Ala Pro Cys
1               5                   10                  15

Gly Leu Leu Leu Asn Leu Thr Gly Thr Leu Ala Pro Gly Trp Arg Leu
            20                  25                  30

Val Lys Gly Phe Leu Asn Gln Pro Val Asp Val Glu Leu Tyr Gln Gly
        35                  40                  45

Leu Trp Asp Met Cys Arg Glu Gln Ser Ser Arg Glu Arg Glu Cys Gly
    50                  55                  60

Gln Thr Asp Gln Trp Gly Tyr Phe Glu Ala Gln Pro Val Leu Val Ala
65                  70                  75                  80

Arg Ala Leu Met Val Thr Ser Leu Ala Ala Thr Val Leu Gly Leu Leu
                85                  90                  95

Leu Ala Ser Leu Gly Val Arg Cys Trp Gln Asp Glu Pro Asn Phe Val
            100                 105                 110

Leu Ala Gly Leu Ser Gly Val Val Leu Phe Val Ala Gly Leu Leu Gly
        115                 120                 125

Leu Ile Pro Val Ser Trp Tyr Asn His Phe Leu Gly Asp Arg Asp Val
    130                 135                 140

Leu Pro Ala Pro Ala Ser Pro Val Thr Val Gln Val Ser Tyr Ser Leu
145                 150                 155                 160

Val Leu Gly Tyr Leu Gly Ser Cys Leu Leu Leu Gly Gly Phe Ser
                165                 170                 175

Leu Ala Leu Ser Phe Ala Pro Trp Cys Asp Glu Arg Cys Arg Arg Arg
            180                 185                 190

Arg Lys Gly Pro Ser Ala Gly Pro Arg Arg Ser Ser Val Ser Thr Ile
        195                 200                 205

Gln Val Glu Trp Pro Glu Pro Asp Leu Ala Pro Ala Ile Lys Tyr Tyr
    210                 215                 220

Ser Asp Gly Gln His Arg Pro Pro Ala Gln His Arg Lys Pro Lys
225                 230                 235                 240

Pro Lys Pro Lys Val Gly Phe Pro Met Pro Arg Pro Arg Pro Lys Ala
                245                 250                 255

Tyr Thr Asn Ser Val Asp Val Leu Asp Gly Glu Gly Trp Glu Ser Gln
            260                 265                 270

Asp Ala Pro Ser Cys Ser Thr His Pro Cys Asp Ser Ser Leu Pro Cys
        275                 280                 285

Asp Ser Asp Leu
    290
```

<210> SEQ ID NO 7
<211> LENGTH: 1754
<212> TYPE: DNA
<213> ORGANISM: Mus musculus

<400> SEQUENCE: 7

```
gagtggggac agttccgcgc gagagacaaa gagcgcccag agagcgcagc gagcatcgct    60
```

| | |
|---|---|
| gctacccagc ccggcaacct cgcagattcg aggacagggt gcgcagcgga gcagccacag | 120 |
| ctgctaggga cccaagaggc tacgcaggat gcggacgccg gtggtgatga cgctgggcat | 180 |
| ggtgctcacg ccctgcgggt tgctgcttaa tcttgtcagt acactggccc cgggctggcg | 240 |
| gctggtgaag ggctttctgg accagccagt ggacgtggtg ctgtaccagg gctgtgggga | 300 |
| catatgtcgc gagcagagca gtcgcgaacg cgagtgcggc cagcccgacg agtggaacta | 360 |
| cttccagacc cagcctgtgc aggtggcccg gggactcatg atcacgtcac tggccactac | 420 |
| cgccctaggg ctgctgctgg cttccctcgg tgtgcgctgt tggcaagatg agccccacta | 480 |
| cgggctagcg ggcctctctg gcgtggtgtt tttcgtcgct ggcctcttca gcctcatccc | 540 |
| ggtctcctgg tataaccact tcttgtcaga tcccgacgtc ctggccgccc cgagctcgcc | 600 |
| ggtcacggtg caggtcagct acagcctggt gctgggctac ctaggcagct gcctgctgct | 660 |
| tctgggcggc ttctctctgg cgctcagctt tgcgccctgg tgtgaagagc gttgtcgccg | 720 |
| ctgtcgcaag gcgcccccag caggcccgcg ccgcagcagc atcagcaccg tctacgtgga | 780 |
| ctggccggaa ccagcgctca cacctgccat caagtactac agcgacggac agcatcggcc | 840 |
| tcctcccacc gcagagcaca gggacaccag caagctcaag gttggattcc cgatgccacg | 900 |
| accgccaccc aagtcctaca ccaacccgat ggatgtgctt gagggagaag aaaagaagac | 960 |
| agccacctcc caaggtggtt cctcctctcg cagcactcgg ccctgccaaa attcgctgcc | 1020 |
| ctgtgactcc gacctgtaga cagggttcac ctgagctctg cctggagtct gagggtgact | 1080 |
| tgaacttctg ccagtacatc tgcaactaga accctggtcg ccttcctcta actggagggc | 1140 |
| aagccttcct tttctagggc caaactcctc tccaaatact aggttgggtt catttatctt | 1200 |
| ttaaggagtt ttacttttct ctccagaggg accaggtctt cttatgcagt gacaagagtg | 1260 |
| cgtagtgttt tctttgcata ctgttcatcg cagtagcaac aaaattgcaa tcagccaaca | 1320 |
| ggctttaaaa cgtccctgaa cgtacagtat tctaagttac cgtgagcctt cacaaacatc | 1380 |
| attctcgagg ttttttgctt ttctccctgc ttcagtctcc agagaacata aatggccaaa | 1440 |
| aatgttaagt ctggctatat ttgaaggtta tgacataaag ccagcagctt taatggcttt | 1500 |
| tatgaagtga agtgacttgt ttaactccta tttatatttc tctgtgcata tatagtattt | 1560 |
| atcttttcta atcacttgtt tctgtgtagg aggttgagct tgtcttccaa aagccaaggc | 1620 |
| gatgctacac tgtcctgttc ccgagatacc tcgccctgaa cagagatata ttttgtacaa | 1680 |
| aatgaactgt taagttgcct ttggctaaca tccatatgta tatatcttat ttataaataa | 1740 |
| aaattgtaaa tgcc | 1754 |

<210> SEQ ID NO 8
<211> LENGTH: 296
<212> TYPE: PRT
<213> ORGANISM: Mus musculus

<400> SEQUENCE: 8

Met Arg Thr Pro Val Met Thr Leu Gly Met Val Leu Thr Pro Cys
1               5                   10                  15

Gly Leu Leu Leu Asn Leu Val Ser Thr Leu Ala Pro Gly Trp Arg Leu
            20                  25                  30

Val Lys Gly Phe Leu Asp Gln Pro Val Asp Val Leu Tyr Gln Gly
        35                  40                  45

Leu Trp Asp Ile Cys Arg Glu Gln Ser Ser Arg Glu Arg Glu Cys Gly
    50                  55                  60

Gln Pro Asp Glu Trp Asn Tyr Phe Gln Thr Gln Pro Val Gln Val Ala

-continued

```
                 65                  70                  75                  80
Arg Gly Leu Met Ile Thr Ser Leu Ala Thr Thr Ala Leu Gly Leu Leu
                 85                  90                  95
Leu Ala Ser Leu Gly Val Arg Cys Trp Gln Asp Glu Pro His Tyr Gly
                100                 105                 110
Leu Ala Gly Leu Ser Gly Val Val Phe Phe Val Ala Gly Leu Phe Ser
                115                 120                 125
Leu Ile Pro Val Ser Trp Tyr Asn His Phe Leu Ser Asp Pro Asp Val
                130                 135                 140
Leu Ala Ala Pro Ser Ser Pro Val Thr Val Gln Val Ser Tyr Ser Leu
145                 150                 155                 160
Val Leu Gly Tyr Leu Gly Ser Cys Leu Leu Leu Gly Gly Phe Ser
                165                 170                 175
Leu Ala Leu Ser Phe Ala Pro Trp Cys Glu Arg Cys Arg Arg Cys
                180                 185                 190
Arg Lys Ala Pro Pro Ala Gly Pro Arg Arg Ser Ser Ile Ser Thr Val
                195                 200                 205
Tyr Val Asp Trp Pro Glu Pro Ala Leu Thr Pro Ala Ile Lys Tyr Tyr
                210                 215                 220
Ser Asp Gly Gln His Arg Pro Pro Thr Ala Glu His Arg Asp Thr
225                 230                 235                 240
Ser Lys Leu Lys Val Gly Phe Pro Met Pro Arg Pro Pro Lys Ser
                245                 250                 255
Tyr Thr Asn Pro Met Asp Val Leu Glu Gly Glu Lys Lys Thr Ala
                260                 265                 270
Thr Ser Gln Gly Gly Ser Ser Ser Arg Ser Thr Arg Pro Cys Gln Asn
                275                 280                 285
Ser Leu Pro Cys Asp Ser Asp Leu
                290                 295

<210> SEQ ID NO 9
<211> LENGTH: 26
<212> TYPE: DNA
<213> ORGANISM: Artificial
<220> FEATURE:
<223> OTHER INFORMATION: oligonucleotide primer

<400> SEQUENCE: 9
aagaggctac gcaggatgcg gacgcc                                      26

<210> SEQ ID NO 10
<211> LENGTH: 27
<212> TYPE: DNA
<213> ORGANISM: Artificial
<220> FEATURE:
<223> OTHER INFORMATION: oligonucleotide primer

<400> SEQUENCE: 10
ctgtctacag gtcggagtca cagggca                                     27
```